United States Patent

Matsumura et al.

[11] Patent Number: 4,923,984
[45] Date of Patent: May 8, 1990

[54] PYRROLO(1,4)BENZODIAZEPINE DERIVATIVES

[75] Inventors: Hiromu Matsumura, Hyogo; Hiroshi Hashizume, Osaka; Akira Matsushita, Hyogo; Masami Eigyo, Nara, all of Japan

[73] Assignee: Shionogi & Co., Ltd., Osaka, Japan

[21] Appl. No.: 386,946

[22] Filed: Jul. 31, 1989

[30] Foreign Application Priority Data

Aug. 5, 1988 [JP] Japan .................. 63-196354

[51] Int. Cl.⁵ .................................. C07D 413/06
[52] U.S. Cl. .................................... 540/496
[58] Field of Search ................. 540/496; 514/220

[56] References Cited

U.S. PATENT DOCUMENTS 4,118,396 10/1978 Pifferi et al. .................. 548/538
4,369,138 1/1983 Kyburz et al. ................. 548/539

FOREIGN PATENT DOCUMENTS 25277 6/1974 Japan ........................ 540/496
1039113 8/1966 United Kingdom .

OTHER PUBLICATIONS

Foye Principals of Medicinal Chemistry (Philadelphia, Lea and Febiger 1976) 230-236.

Primary Examiner—Mukund J. Shah
Assistant Examiner—E. C. Ward
Attorney, Agent, or Firm—Birch, Stewart, Kolasch & Birch

[57] ABSTRACT

A compound of the formula:

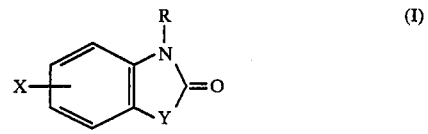

wherein Y is

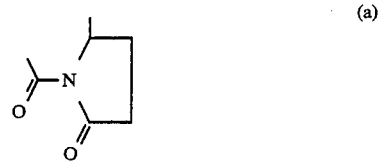

or

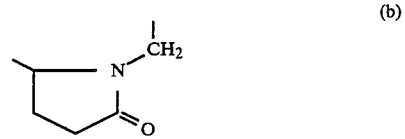

R is hydrogen, $C_1$–$C_5$ alkyl, $C_1$–$C_5$ alkanoyl, or $C_7$–$C_9$ phenylalkyl, and X is hydrogen, $C_1$–$C_5$ alkoxy, or halogen being useful for the treatment of senile dementia, psychoneurosis, and/or amnesia.

23 Claims, No Drawings

PYRROLO(1,4)BENZODIAZEPINE DERIVATIVES

BACKGROUND OF THE INVENTION

1. Field of the Invention

This invention relates to novel pyrrolo[1,4]benzodiazepine derivatives.

2. Prior Art

Studies of γ-aminobutyric acid (GABA) and its derivatives or acetylcholine and its derivatives have heretofore been performed in order to supply a drug for treatment of cerebral insufficiency. On the way of these studies, piracetam, namely 2-oxo-1-pyrrolidineacetoamide (GB Pat. No. 1,039,113) was developed, but this drug was not found so effective in fact as to be expected at the beginning.

Further U.S. Pat. Nos. 4,118,396 and 4,369,139 disclose some pyrrolidone derivatives useful in the prevention of cerebral insufficiency.

SUMMARY OF THE INVENTION

This invention relates to novel benzodiazepine derivatives. More particularly, this invention is directed to pyrrolo[1,4]benzodiazepine derivatives which have been found to be particularly available as a drug for treatment of senile dementia, psychoneurosis, and/or amnesia, to their preparation, to their use and to pharmaceutical formulations containing the compounds.

DETAILED DESCRIPTION

This invention relates to compounds of the formula:

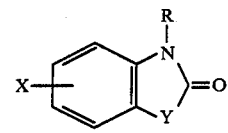

wherein Y is

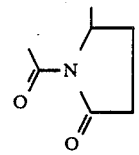

or

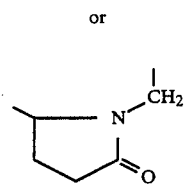

R is hydrogen, $C_1$–$C_5$ alkyl, $C_1$–$C_5$ alkanoyl, or $C_7$–$C_9$ phenylalkyl, and X is hydrogen, $C_1$–$C_5$ alkoxy, or halogen or its pharmaceutically acceptable acid addition salts.

In the specification, $C_1$–$C_5$ alkyl means straight or branched chain $C_1$–$C_5$ alkyl, including methyl, ethyl, n-propyl, isopropyl, n-butyl, sec-butyl, isobutyl, tert-butyl, n-pentyl, isopentyl, tert-pentyl, and the like.

$C_1$–$C_5$ alkanoyl means formyl, acetyl, propionyl, butyryl, isobutyryl, valeryl, and isovaleryl.

$C_1$–$C_5$ alkoxy means methoxy, ethoxy, propoxy, butoxy, and pentoxy.

$C_7$–$C_9$ phenylalkyl means benzyl, phenethyl, and phenylpropyl.

Synthesis of the compound (I) of the present invention is shown as follows:

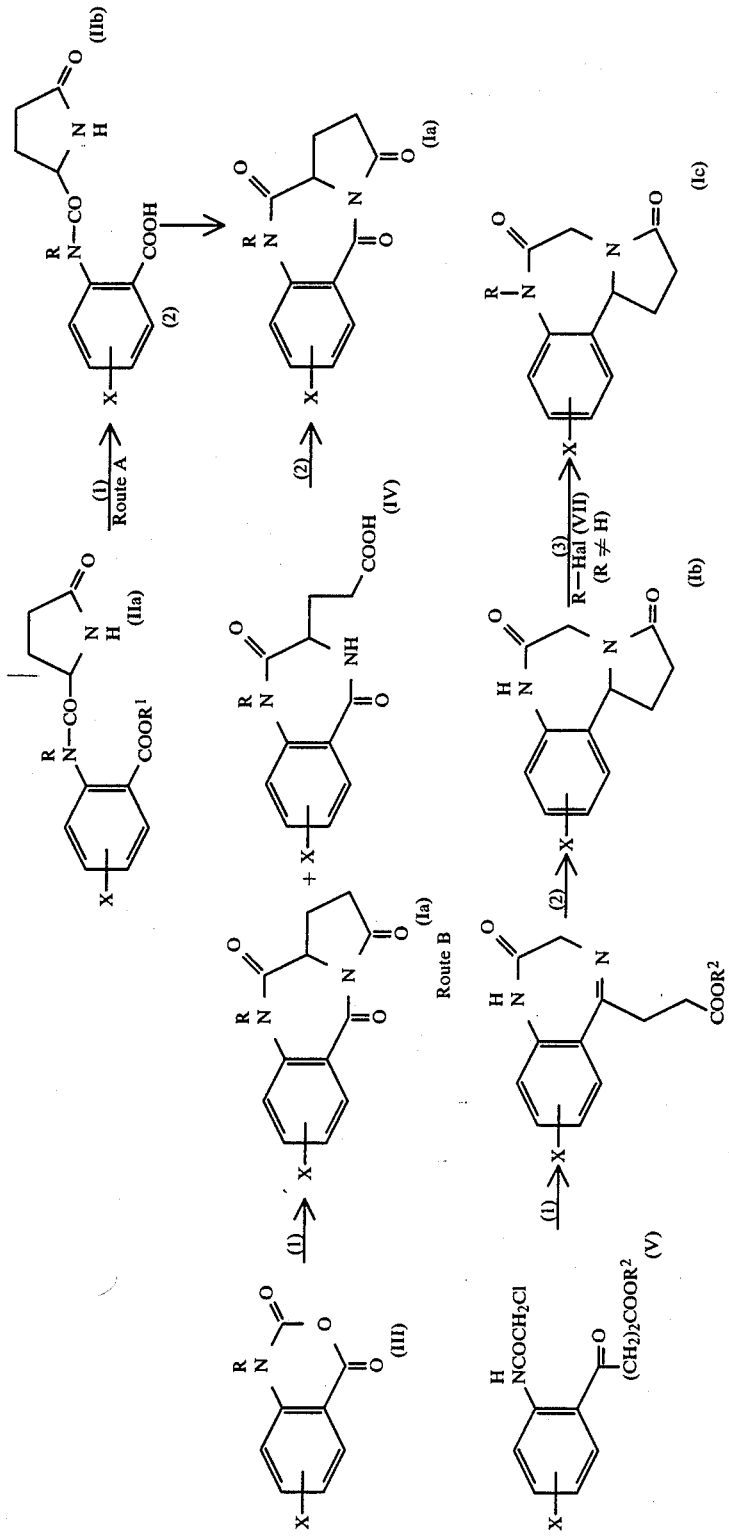
wherein $R^1$ and $R^2$ each is alkyl, Hal is halogen, and R and X have the same meanings as defined above.

Route A (1) The compound (IIb) is prepared by hydrolyzing the compound (IIa) in an appropriate solvent in the presence of an appropriate base. As the solvent, water, aqueous alcohol such as aqueous methanol or aqueous ethanol, and a mixture of an organic solvent such as ethyl acetate, acetonitrile, benzene, DMSO, DMF, chloroform, etc. with water are exemplified. As the base, inorganic bases such as sodium hydroxide, potassium hydroxide, sodium carbonate, potassium carbonate, etc. are exemplified. This reaction can be performed at 0°–80° C., preferably at room temperature (1°–30° C.).

(2) The compound (Ia) is prepared by dehydrating the compound (IIb). The reaction can be performed at the temperature from room temperature to 200° C., preferably at about 90° C. in an appropriate solvent in the presence of a dehydrating agent. As the solvent, alcohols, ethyl acetate, acetonitrile, benzene, DMSO, DMF, chloroform, THF, etc. are exemplified. The dehydrating agents include conc. sulfuric acid, phosphorus pentoxide, acetic anhydride, acetyl chloride, DCC, etc.

The starting material (IIa) can be prepared in the following scheme.

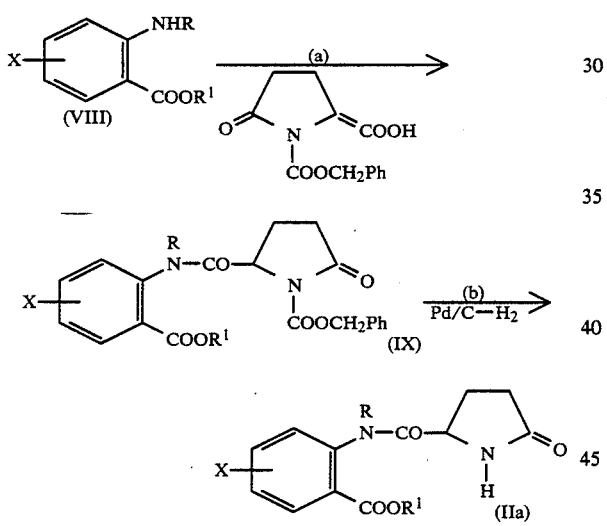

wherein R, R$^1$ and X have the same meanings as defined above.

(a) The compound (IX) is prepared by condensing alkyl anthranilate (VIII) with N-benzyloxycarbonyl-pyrroglutamic acid in an appropriate solvent such as THF, dichloromethane, or DMSO in a conventional manner at 10°–150° C., preferably at room temperature.

(b) The starting material (II) is prepared by hydrogenating the compound (IX) in the presence of Pd-C at room temperature in a solvent such as methanol, ethanol, THF etc. for removal of N-benzyloxycarbonyl group.

Route B

Alternatively the compound (Ia) can be prepared by reacting the starting compound (III) with glutamic acid in the presence of a base. The reaction is carried out in the presence of a base (e.g. triethylamine, pyridine, dimethylaniline) in hydrous solvent (e.g. hydrous THF, dioxane, DMSO, etc.) at room temperature. During the reaction, the compound (IV) is produced as an intermediate other than (Ia) and can be converted into the compound (Ia) by dehydrating with acetic anhydride/acetic acid under heating. The reaction is performed at temperature from 110° to 140° C.

The starting material (III) can be synthesized in the process as described in P. W. Sadler, J. Org. Chem., 21, 169 (1956).

Route C (1) The compound (VI) is prepared by reacting the compound (V) with NaI and ammnonium carbonate in an appropriate solvent at 10°–120° C., preferably at room temperature. The solvent includes acetonitrile, benzene, toluene, methanol, ethanol, DMSO, and THF.

The starting material (V) can be prepared as in the following scheme.

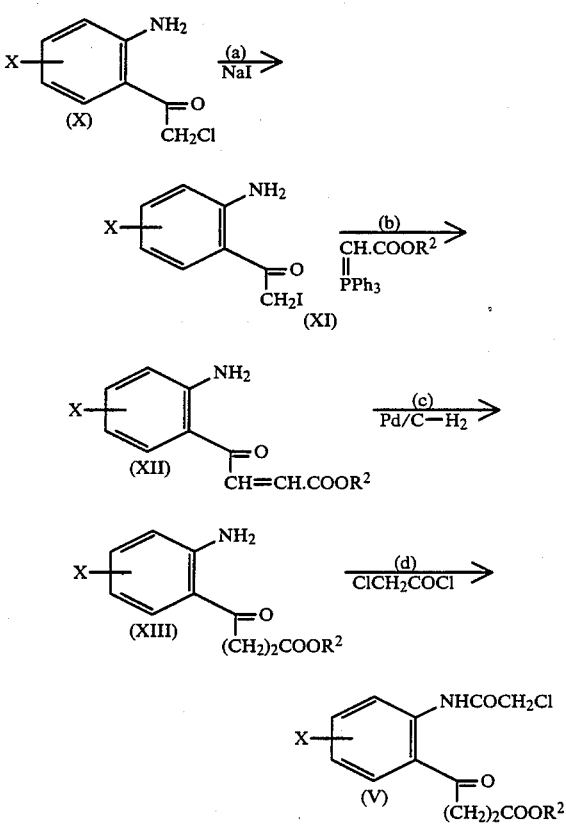

wherein R$^2$ and X have the same meanings as defined above.

(a) The compound (X) is allowed to react with NaI in an organic solvent at 10°–150° C., preferably at room temperature to give the compound (X I). As an organic solvent, acetonitrile, benzene, and DMSO are exemplified.

(b) The compound (X I) is allowed to react with triphenylphosphine carbomethoxymethylene in an organic solvent at room temperature to give the compound (X II). As an organic solvent acetonitrile, toluene, and benzene are exemplified.

(c) The compound (X II) is hydrogenated in the presence of Pd-C at room temperature in an appropriate solvent to give the compound (X III). As an appropriate solvent, acetonitrile, benzene, methanol, ethanol, DMSO, and THF are exemplified.

(d) The compound (X III) is allowed to react with chloroacetyl chloride in an appropiate solvent at room temperature to give the compound (V). As an appropriate solvent, methanol, ethanol, and methylene chloride are exemplified.

(2) The compound (VI) is subjected to cyclization with NaBH₃CN at room temperature in an appropriate solvent. As an appropriate solvent, acetic acid, acetonitrile, methanol, and ethanol are exemplified. The reaction will be accelerated by heating at 30° to 60° C.

(3) The compound (Ib) is allowed to react with the halide (VII) in an appropriate solvent in the presence of an appropriate base at 10°–150° C., preferably at room temperature to give the compound (Ic). The solvent includes benzene, DMSO, DMF, chloroform, ethyl acetate, and THF. The base includes sodium hydride, triethylamine, and pyridine.

In accordance with the process of the present invention as described above, the compounds of the formula:

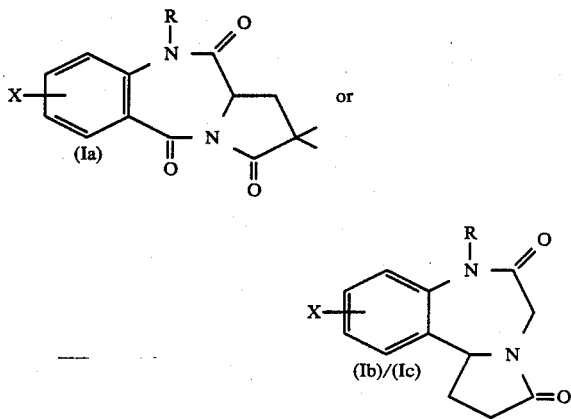

wherein R is hydrogen, $C_1$–$C_3$ alkyl, $C_1$–$C_3$ alkanoyl, or benzyl, and X is hydrogen, halogen, or $C_1$–$C_3$ alkanoyl are preferably prepared.

More concretely, this invention includes the following compounds:

5-acetyl-1H-pyrrolo[2,1-c][1,4]benzodiazepine-1,4,10-trione;
5-methyl-1H-pyrrolo[2,1-c][1,4]benzodiazepine-1,4,10-trione;
5-propyl-1H-pyrrolo[2,1-c][1,4]benzodiazepine-1,4,10-trione;
5-benzyl-1H-pyrrolo[2,1-c][1,4]benzodiazepine-1,4,10-trione;
7-methoxy-5-methyl-1H-pyrrolo[2,1-c][1,4]benzodiazepine-1,4,10-trione;
5-benzyl-7-methoxy-1H-pyrrolo[2,1-c][1,4]benzodiazepine-1,4,10-trione;
7-fluoro-5-methyl-1H-pyrrolo[2,1-c][1,4]benzodiazepine-1,4,10-trione;
5-benzyl-7-fluoro-1H-pyrrolo[2,1-c][1,4]benzodiazepine-1,4,10-trione;
7-methoxy-1H-pyrrolo[2,1-c][1,4]benzodiazepine-1,4,10-trione;
10-chloro-7,11b-dihydro-1H-pyrrolo[1,2-d][1,4]benzodiazepine-3,6-(2H,5H)-dione;
10-chloro-7-methyl-7,11b-dihydro-1H-pyrrolo[1,2-d][1,4]benzodiazepine-3,6-(2H,5H)-dione;
10-chloro-7-n-propyl-7,11b-dihydro-1H-pyrrolo[1,2-d][1,4]benzodiazepine-3,6-(2H,5H)-dione;
7-benzyl-10-chloro-7,11b-dihydro-1H-pyrrolo[1,2-d][1,4]benzodiazepine-3,6-(2H,5H)-dione;
10-fluoro-7,11b-dihydro-1H-pyrrolo[1,2-d][1,4]benzodiazepine-3,6-(2H,5H)-dione;
10-fluoro-7-n-propyl-7,11b-dihydro-1H-pyrrolo[1,2-d][1,4]benzodiazepine-3,6-(2H,5H)-dione;
7-benzyl-10-fluoro-7,11b-dihydro-1H-pyrrolo[1,2-d][1,4]benzodiazepine-3,6-(2H,5H)-dione;
7,11b-dihydro-7-n-propyl-1H-pyrrolo[1,2-d][1,4]benzodiazepine-3,6-(2H,5H)-dione;
7,11b-dihydro-7-n-propyl-1H-pyrrolo[1,2-d][1,4]benzodiazepine-3,6-(2H,5H)-dione; and
7,11b-dihydro-7-methyl-1H-pyrrolo[1,2-d][1,4]benzodiazepine-3,6-(2H,5H)-dione.

Furthermore, the compound (I) of the present invention can be synthesized in a conventional manner known as the synthetic process of a similar compound in the chemical literature.

For example, the compound (I) may be orally administered in the form of tablets, grannules, powder, capsules or liquid, or parenterally as injections or suppositories.

These preparations are manufactured in a conventional manner by using additives such as diluents, binders, disintegrators, lubricants, stabilizers, corrigents, suspenders, dispersants, solubilizers, and antiseptics.

Examples of the diluents are lactose, sucrose, starch, cellulose, and sorbit; examples of the binders are gum arabic, gelatin, and polyvinylpyrrolidine; and examples of the lubricants are magnesium stearate, talc, and silica gel, respectively.

When the objective compound (I) of the present invention is used for the treatment of senile dementia, psychoneurosis, and/or amnesia, suitable daily doses are 0.01–20 mg/kg for oral administration and 0.05–50 mg/kg for injection once or in several divisions.

Presently preferred and practical embodiments of this invention are illustratively shown below by Examples, Reference Examples, and Formulations.

The abbreviations used in the Examples, Reference Examples, and Tables have following meanings.

Me: methyl; MeO: methoxy
Et: ethyl; MeOH: methanol
Ac: acetyl; AcOH: acetic acid
Et₂O: ether; Et₃N: triethylamine
Ph: phenyl; DMF: N,N-dimethylformamide
DMSO: dimethyl sulfoxide; THF: tetrahydrofuran
DCC: N,N'-dicyclohexylcarbodiimide
DMA: N,N-dimethylacetamide
HOBT: hydroxybenzotriazole
EEDQ: N-ethoxycarbonyl-2-ethoxy-1,2-dihydroquinoline
d: diluted

EXAMPLE 1

5-Acetyl-1H-pyrrolo[2,1-c][1,4]benzodiazepine-1,4,10-trione (I a-1)

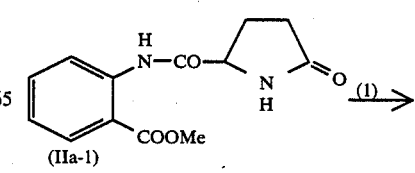

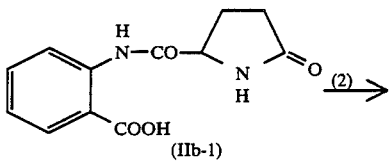

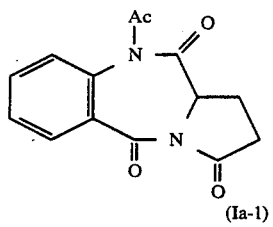

(1) Synthesis of N-(2-carboxyphenyl)-2-oxopyrrolidine-5-carboxyamide (II b-1)

To a solution of 1.794 g (6.840 mM) of the compound (II a-1) in 18 ml of methanol is added 7 ml of 3 N NaOH, and the mixture is stirred at room temperature for 55 min. and concentrated under reduced pressure to give a residue. The residue is mixed with water, and the solution is washed with ethyl acetate and acidified with HCl. The resulting crystals are collected by filtration, washed with water and Et$_2$O, and dried to give 1.57 g (Yield: 92.5%) of the objective compound (II b-1) as crystals.

NMR (90MHz) δ (d$_6$-DMSO): 1.90-2.60 (m, 4H); 4.20 (q, 1H); 7.1-7.7 (m, 2H); 8.05 (d-d, J$_1$=9 Hz, J$_2$=2 Hz, 1H); 8.57 (d, J=9 Hz, 1H)

(2) Synthesis of the Compound I a-1

A mixture of 770 mg (3.102 mM) of N-(2-carboxyphenyl)-2-oxopyrrolidine-5-carboxyamide (II b-1) and 13.9 ml of acetic anhydride is heated at 90° C. for 26 hr. The insoluble material is filtered off and the filtrate is concentrated to give a residue. The residue is chromatographed on a column of silica gel (67 g), eluting with benzene-acetone (9:1 v/v) to give 872 mg of a foamy light yellow product. The compound obtained above is recrystallized from benzene-Et$_2$O to give 345 mg (Yield: 40.9%) of the objective compound (I a-1) melting at 110°-111° C. as colorless needles.

[α]$_D^{22.0}$ −47.2°±0.9° (c=1.006, CHCl$_3$)

Anal. Calcd. (%) for C$_{14}$H$_{12}$N$_2$O$_4$: C, 61.76; H, 4.44; N, 10.29

Found (%): C, 61.75; H, 4.54; N, 10.31

IR ν (CHCl$_3$): 1756, 1708, 1653, 1612, 1580, 1479, 1470, 1418 cm$^{-1}$

NMR (90MHz) δ (CDCl$_3$): 2.10-2.90 (m); 2.57 (s, 7H); 5.10-5.45 (m, 1H); 7.28-8.25 (m, 4H)

EXAMPLE 2

5-Methyl-1H-pyrrolo[2,1-c][1,4]benzodiazepine-1,4,10-trione (I a-2)

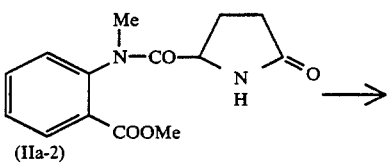

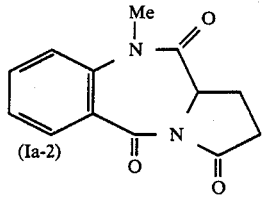

To a solution of 2.482 g (8.983 mM) of N-(2-methoxycarbonylphenyl)-N-methyl-2-oxopyrrolidine-5-carboxyamide (II a-2) in 24 ml of methanol is added 9 ml of 3N NaOH, and the mixture is stirred at room temperature for 15 minutes and 1 hour. The reaction mixture is concentrated to give a residue, which is mixed with water and washed with ethyl acetate. The aqueous layer is acidified with HCl, and extracted with ethyl acetate and then CHCl$_3$-methanol (4:1 v/v). The extract is dried and concentrated to give a residue (II b-2). The residue is mixed with 34 ml of acetic anhydride, and the mixture is heated at 90° C. for 1.5 hr. and concentrated to give a residue. The residue is chromatographed on a column of silica gel (117.6 g), eluting with benzeneacetone (5:1 v/v) to give 1.091 g of the compound (I a-2). This is recrystallized from acetone-ether to give 857 mg (Yield: 46.6%) of the objective compound (I a-2) melting at 152°-153° C. as prisms.

[α]$_D^{22.0}$ +555.3°±5.9° (c=1.015, CHCl$_3$)

Anal. Calcd. (%) for C$_{13}$H$_{12}$N$_2$O$_3$: C, 63.93; H, 4.95; N, 11.47

Found (%): C, 64.02; H, 5.06; N, 11.40

IR ν (CHCl$_3$): 1776, 1673, 1603, 1579, 1489, 1473, 1455, 1422 cm$^{-1}$ NMR (90MHz) δ (CDCl$_3$): 1.8-3.1 (m, 4H); 3.44 (3H, s); 4.54 (d, J=9 Hz, 1H); 7.2~8.0 (m, 4H)

EXAMPLE 3

5-Propyl-1H-pyrrolo[2,1-c][1,4]benzodiazepine-1,4,10-trione (I a-3)

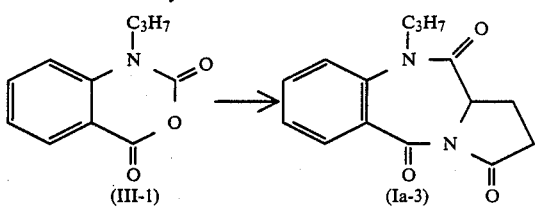

A mixture of 2.053 g (10.004 mM) of N-propylisatoic anhydride (III-1), 1.472 g (10.004 mM) of L-glutamic acid, and 2.791 ml (20.008 mM) of Et$_3$N in water (9.75 ml)-THF (2ml) is allowed to stand at room temperature for 24 hr. After evaporating the solvent under reduced pressure, the residue is dissolved in CHCl$_3$, and the organic layer is dried and concentrated. A mixture (46 ml) of acetic anhydride-acetic acid (1:1 v/v) is added to the resulting residue and the mixture is refluxed for 30 min. and concentrated under reduced pressure to give a residue, which is dissolved in CHCl$_3$. The organic layer is washed with d-HCl, water, aqueous NaHCO$_3$, and water in order, dried and concentrated to give a residue. The residue (2.553 g) is chromatrahed on a column of silica gel (155.8 g), eluting with acetone-benzene (5:1 v/v) to give 1.599 g of a foamy product. This is recrystallized from acetone-ether to give 1.02 g (Yield: 37.4%)

of the objective compound (I a-3) melting at 155°–156° C. as prisms.

$[\alpha]_D^{22.0} +526.9° \pm 5.6°$ (c=1.013, CHCl$_3$)

Anal. calcd. (%) for C$_{15}$H$_{16}$N$_2$O$_3$: C, 66.16; H, 5.92; N, 10.29

Found (%): C, 66.24; H, 6.09; N, 10.25

IR $\nu$ (CHCl$_3$): 1774, 1673, 1602, 1578, 1487, 1457, 1399 cm$^{-1}$

NMR (90MHz) $\delta$ (CDCl$_3$): 0.82 (t, J=7 Hz, 3H); 1.3–3.0 (m, 6H); 3.45–4.40 (m, 2H); 4.52 (d, J=9 Hz, 1H); 7.27–7.95 (m, 4H)

EXAMPLE 4

5-Benzyl-1H-pyrrolo[2,1-c][1,4]benzodiazepine-1,4,10-trione (I a-4)

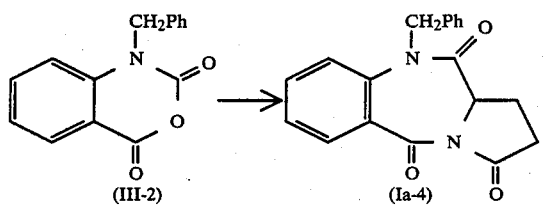

A mixture of 2.00 g (7.897 mM) of N-benzylisatoic anhydride (III-2), 1.162 g (7.897 mM) of L-glutamic acid, and 2.203 ml (15.794 mM) of Et$_3$N in water (7.7 ml)-THF (2 ml) is allowed to stand at room temperature for 21.5 hr. and concentrated under reduced pressure to give a residue, which is added with CHCl$_3$—MeOH. The reaction mixture is filtered to remove insoluble materials, dried and concentrated to give a residue. A mixture (37 ml) of acetic anhydride-acetice acid (1:1 v/v) is added to the residue and the mixture is refluxed under heating for 30 minutes and concentrated under reduced pressure to give a residue. The residue is added with CHCl$_3$, and the mixture is washed with d-HCl, water, aqueous NaHCO$_3$, water in order, dried, and concentrated to give a residue. The residue is treated with Et$_2$O to give 1.9 g (Yield: 75.0%) of crystals. These are recrystallized from acetone-Et$_2$O to give 1.75 g (Yield: 69.2%) of the objective compound (I a-4) melting at 218°–219° C. as prisms.

$[\alpha]_D^{22.0} +434.1° \pm 4.7°$ (c=1.014, CHCl$_3$)

Anal. Calcd. (%) for C$_{19}$H$_{16}$N$_2$O$_3$: C, 71.24; H, 5.03; N, 8.74

Found (%): C, 71.48; H, 5.10; N, 8.80

IR $\nu$ (CHCl$_3$): 1776, 1678, 1604, 1579, 1499, 1488, 1457, 1398 cm$^{-1}$

NMR (90MHz) $\delta$ (CDCl$_3$): 2.0–2.9 (m, 4H); 4.62 (d, J=8 Hz, 1H); 5.09 (s, 2H); 7.1–7.9 (m, 9H)

EXAMPLE 5

5-Methyl-7-methoxy-1H-pyrrolo[2,1-c][1,4]benzodiazepine-1,4,10-trione (I a-5)

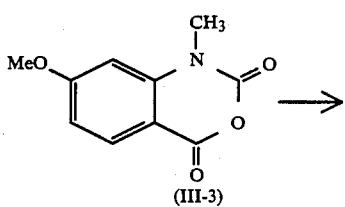

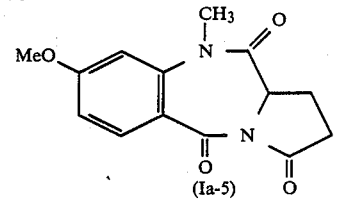

A mixture of 2.130 g (10.281 mM) of N-methyl-4-methoxyisatoic anhydride (III-3), 1.513 g (10.281 mM) of L-glutamic acid, and 2.87 ml (20.562 mM) of Et$_3$N in water (9.8 ml)-THF (2.6 ml) is allowed to stand at room temperature for 23 hr. and concentrated under reduced pressure to give a residue. The residue is dissolved in CHCl$_3$—MeOH (4:1 v/v), dried, and concentrated to give a residue. The residue is added with a solution (48 ml) of acetic anhydride-acetic acid (1:1 v/v), and the mixture is refluxed for 10 min. and concentrated under reduced pressure. The residue is dissolved in CHCl$_3$, and the organic layer is washed with d-HCl, water, aqueous NaHCO$_3$, and water in order, dried and concentrated. The resulting residue (2.501 g) is chromatographed on a column of silica gel (111.9 g), eluting with acetone-benzene (1:3 v/v) to give 1.630 g of a foamy product, which is recrystallized from acetone-Et$_2$O to give 1.02 g (Yield: 32.6%) of the objective compound melting at 139°–140° C. as prisms.

$[\alpha]_D^{24.0} +448.3° \pm 4.8°$ (c=1.016, CHCl$_3$)

Anal. Calcd. (%) for C$_{14}$H$_{14}$N$_2$O$_4$·½CH$_3$COCH$_3$: C, 61.38; H, 5.65; N, 9.24

Found (%): C, 61.35; H, 5.57; N, 9.47

IR $\nu$ (CHCl$_3$): 1771, 1711, 1684, 1669, 1609, 1571, 1502, 1474, 1465, 1446, 1437, 1424 cm$^{-1}$

NMR (90MHz), $\delta$ (CDCl$_3$): 2.14 (s, 3H); 2.0–2.9 (m, 4H); 3.41 (s, 3H); 3.98 (s, 3H); 4.52 (d, J=9 Hz, 1H); 6.70 (d, J=2 Hz, 1H); 6.85 (dd, J$_1$=9 Hz, J$_2$=2 Hz, 1H); 7.89 (d, J=9 Hz, 1H)

EXAMPLE 6

5-Benzyl-7-methoxy-1H-pyrrolo[2,1-c][1,4]benzodiazepine-1,4,10-trione (I a-6)

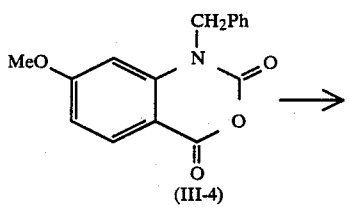

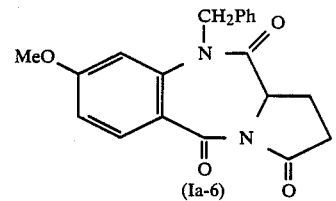

A mixture of 4.758 g (16.796 mM) of N-benzyl-4-methoxyisatoic anhydride (III-4), 2.471 g (16.796 mM) of L-glutamic acid, and 4.69 ml (33.592 mM) of Et$_3$N in water (16 ml)-THF (4.2 ml) is allowed to stand at room temperature for 27.5 hr. and concentrated under reduced pressure to give a residue, which is dissolved in CHCl$_3$. The organic layer is dried and concentrated to give a residue. The residue is mixed with 78 ml of acetic anhydrideacetic acid (1:1 v/v), and the mixture is refluxed for 10 min. After evaporation of the solvent, the resulting residue is dissolved in CHCl₃, and the organic layer is washed with d-HCl, water, aqueous NaHCO₃, and water in order, dried, and concentrated. The residue (5.531 g) is chromatographed on a column of silica gel (172.2 g), eluting with CHCl₃—MeOH (49:1 v/v) to give 3.989 g of a foamy product. This is recrystallized from acetone-Et₂O to give 2.216 g (Yield: 37.6%) of the objective compound (I a-6) melting at 174.5°–176.5° C. as prisms.

$[\alpha]_D^{24.0} +0.8° \pm 0.4°$ (c=1.002, CHCl₃)

Anal. Calcd. (%) for $C_{20}H_{18}N_2O_4$: C, 68.56; H, 5.18; N, 8.00

Found (%): C. 68.69; H, 5.25; N, 7.99

IR ν (CHCl₃): 1771, 1682 (sh), 1672, 1609, 1573, 1499, 1466, 1457, 1446 cm⁻¹

NMR (90MHz) δ (CDCl₃): 1.95–2.95 (m, 4H); 3.72 (s, 3H); 4.65 (d, J=9 Hz, 1H); 5.00, 5.20 (ABq, J=15 Hz, 2H); 6.72 (br, 1H); 6.82 (br.d, J=9 Hz, 1H); 7.25 (br, 5H); 8.85 (d, J=9 Hz, 1H)

EXAMPLE 7

5-Methyl-7-fluoro-1H-pyrrolo[2,1-c][1,4]benzodiazepine-1,4,10-trione (I a-7)

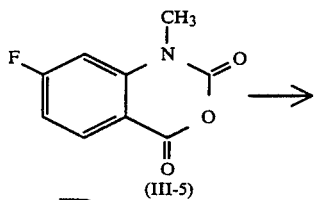
(III-5)

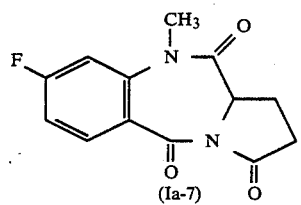
(Ia-7)

A mixture of 3.778 g (19.360 mM) of N-methyl-4-fluoroisatoic anhydride (III-5), 2.848 g (19.360 mM) of L-glutamic acid, and 5.40 ml (38.720 mM) of Et₃N in water (18.4 ml)-THF (4.84 ml) is allowed to stand at room temperature for 19 hr. and concentrated under reduced pressure. The resulting residue is mixed with 90 ml of acetic anhydride-acetic acid (1:1 v/v), and the mixture is refluxed under heating for 10 min. and concentrated under reduced pressure. The resulting residue is mixed with CHCl₃, and the organic layer is washed with d-HCl, water, aqueous NaHCO₃ and water in order, dried, and concentrated. The residue (4.943 g) is chromatographed on a silica gel (174.9 g), eluting with CHCl₃—MeOH (49:1 v/v) to give 3.430 g of a foamy compound. This is recrystallized from CH₂Cl₂-Et₂O to give 2.815 g (Yield: 55.5%) of the objective compound (I a-7) melting at 155.0°–157.0° C. as prisms.

$[\alpha]_D^{24.0} +528.4° \pm 5.6°$ (c=1.014, CHCl₃)

Anal. Calcd. (%) for $C_{13}H_{11}N_2O_3F$: C, 59.54; H, 4.23; N, 10.68; F, 7.24

Found (%): C, 59.31; H, 4.14; N, 10.61; F, 7.37

IR ν (CHCl₃): 1777, 1690, 1678, 1610, 1590, 1507, 1476, 1449, 1433, 1425 cm⁻¹

NMR (90MHz) δ (CDCl₃): 1.95–3.0 (m, 4H); 3.43 (s, 3H); 4.53 (d, J=8 Hz, 1H); 6.9–7.2 (m, 2H); 7.94 (dd, J₁=10 Hz, J₂=7 Hz, 1H)

EXAMPLE 8

5-Benzyl-7-fluoro-1H-pyrrolo[2,1-c][1,4]benzodiazepine-1,4,10-trione (I a-8)

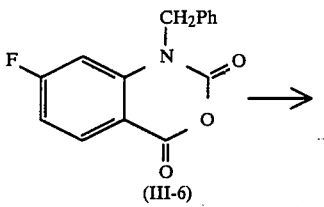
(III-6)

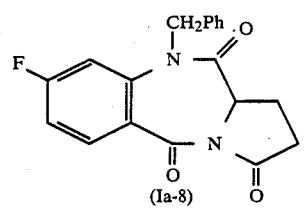
(Ia-8)

A mixture of 1.273 g (41.56 mM) of N-benzyl-4-fluoroisatoic anhydride (III-6), 6.115 g (41.56 mM) of L-glutamic acid, and 11.6 ml (83.12 mM) of Et₃N in water (39.5 ml)-THF (10.4 ml) is allowed to stand at room temperature for 20 hr. and concentrated under reduced pressure. The residue is refluxed under heating and concentrated under reduced pressure. The residue is mixed with 193.2 ml of acetic anhydride-acetic acid (1:1 v/v), and the mixture is refluxed under heating for 10 minutes and concentrated under reduced pressure. The residue is mixed with CHCl₃ and the organic layer is washed with d-HCl, water, aqueous NaHCO₃ and water in order, dried and concentrated. The residue (11.987 g) is chromatographed on a column of silica gel (207.9 g), eluting with CHCl₃—MeOH (49:1 v/v) to give a foamy compound, which is recrystallized from CH₂Cl₂-Et₂O to give 7.992 g (Yield: 56.8%) of the objective compound (I a-8) melting at 195.0–197.0 as scaly crystals.

$[\alpha]_D^{22.0} -0.7° \pm 0.4°$ (c=1.015, CHCl₃)

Anal. Calcd. (%) for $C_{19}H_{15}N_2O_3F$: C, 67.45; H, 4.47; N, 8.28; F, 5.62

Found (%): C, 67.26; H, 4.44; N, 8.25; F, 5.69

IR, ν (CHCl₃): 1776, 1679, 1610, 1588, 1498, 1454, 1437 cm⁻¹

NMR (90 MHz) δ (CDCl₃): 2.0~3.0 (m, 4H); 4.64 (d, J=8 Hz, 1H); 5.11 (s, 2H); 6.90~7.40 (m, 7H); 7.88 (dd, J₁=19 Hz, J₂=8 Hz, 1H)

EXAMPLE 9

7-Methoxy-1H-pyrrolo[2,1-c][1,4]benzodiazepine-1,4,10-trione (I a-9)

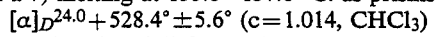
(III-7)

-continued

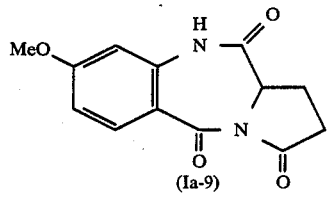

(Ia-9)

A mixture of 2.000 g (10.354 mM) of 4-methoxyisatoic anhydride (III-7), 1.523 g (10.354 mM) of L-glutamic acid, and 2.89 ml (20.708 mM) of Et₃N in water (10 ml)-THF (2.6 ml) is allowed to stand at room temperature for 23 hours and concentrated under reduced pressure. The residue obtained is dissolved in CHCl₃, and the solution is dried and concentrated. The resulting residue is mixed with 48 ml of acetic anhydride-acetic acid (1:1 v/v), and the mixture is refluxed under heating for 60 minutes and concentrated under reduced pressure. The residue is mixed with CHCl₃, and the mixture is washed with d-HCl, water, aqueous NaHCO₃ and water in order, dried and concentrated. The residue (2.148 g) is chromatographed on a column of silica gel (147 g), eluting with a mixture of CHCl₃—MeOH (19:1 v/v) to give a foamy compound. This is recrystallized from CHCl₃ to give 584 mg (Yield: 21.2%) of the objective compound (I a-9) melting at 225°-230° C. as prisms.

$[\alpha]_D^{22.0} -1.2° \pm 0.4°$ (c=1.012, DMSO)

Anal. Calcd. (%) for $C_{13}H_{12}N_2O_4 \cdot 0.3H_2O$: C, 58.78; H, 4.78; N, 10.55

Found (%): C, 58.70; H, 4.48; N, 10.35

IR, ν (CHCl₃): 3283, 3243, 3203, 3165, 3081, 1762, 1697, 1661, 1615, 1575, 1520, 1477, 1463, 1449, 1406 cm⁻¹

NMR (90 MHz) δ (CDCl₃): 1.95–2.95 (m, 4H); 3.84 (s, 3H); 4.50 (d, J=8 Hz, 1H); 6.60 (d, J=2 Hz, 1H); 6.79 (dd, J₁=9 Hz, J₂=2 Hz, 1H); 7.95 (d, J=9 Hz, 1H); 9.32 (br.s, 1H)

EXAMPLE 10 (a)

10-Chloro-7-methyl-7,11b-dihydro-1H-pyrrolo[1,2-d][1,4]benzodiazepine-3,6(2H,5H)-dione (I c-1)

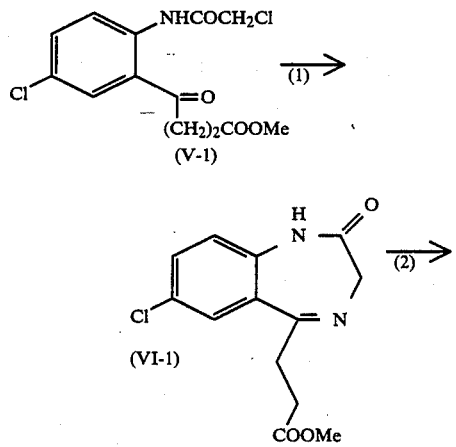

-continued

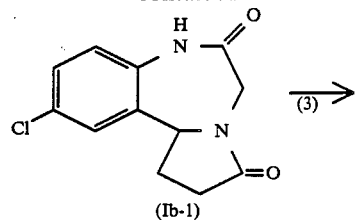

(Ib-1)

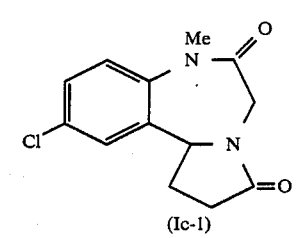

(Ic-1)

(1)
7-Chloro-5-(2-methoxycarbonylethyl)-2H-[1,4]benzodizepine-2-one (VI-1)

To a solution of 253 mg (0.795 mM) of the compound (V-1) in 12 ml of CH₃CN is added a mixture of 143 mg (0.954 mM) of NaI and 600 mg (6.244 mM) of (NH₄)₂CO₃, and the mixture is allowed to stand at room temperature for 3 days. The reaction mixture is concentrated to give a residue, which is poured into aqueous Na₂S₂O₃. The solution is extracted with CH₂Cl₂, and the CH₂Cl₂ layer is washed with saturated brine, dried and concentrated. The resulting residue is chromatographed on a column of silica gel (62.3 g), eluting with CHCl₃—MeOH (49:1 v/v) to give 175 mg (Yield: 73.7%) of the objective compound (VI-1) melting at 113.5°–114.5° C. as crystals.

IR ν (CHCl₃): 3380, 1723, 1681, 1736, 1481, 1439 cm⁻¹

NMR (90 MHz) δ (CDCl₃): 2.72 (t, J=7 Hz, 2H); 3.01 (t, J=7 Hz, 2H); 3.67 (s, 3H); 4.10 (s, 2H); 7.09 (d, J=9 Hz, 1H); 7.40 (d-d, J₁=9 Hz, J₂=2 Hz, 1H); 7.60 (d, J=2 Hz, 1H)

(2)
10-Chloro-7,11b-dihydro-1H-pyrrolo[1,2-d][1,4]benzodiazepine-3,6(2H,5H)-dione (I b-1)

To a solution of 1.0 g (3.562 mM) of the compound (VI-1) in 20 ml of acetic acid is added 471 mg (7.124 mM) of NaBH₃CN under cooling, and the mixture is stirred at room temperature for 3 hr. Then the mixture is concentrated to give a residue, which is washed with ice-water. The residue is basified with aqueous Na₂CO₃ and extracted with CH₂Cl₂. The CH₂Cl₂ layer is washed with saturated brine, and the solution is dried and concentrated to give a blue foamy compound. The foamy compound (1.015 g) obtained is dissolved in 8 ml of acetic acid, and the solution is allowed to stand overnight and concentrated under reduced pressure. The crystalline residue is washed with Et₂O and recrystallized from CHCl₃—MeOH—Et₂O to give 761 mg (Yield: 85.2%) of the compound (I b-1) melting at 242°–243° C. (dec.) as blue needles.

Anal Calcd. (%) for $C_{12}H_{11}ClN_2O_2$: C, 57.50; H, 4.42; N, 11.17; Cl, 14.14

Found (%): C, 57.50; H, 4.51; N, 11.11; Cl, 14.29

IR ν (CHCl₃): 3190, 3075, 1685, 1676(sh), 1483, 1454, 1429, 1418, 1392 cm⁻¹

NMR (200 MHz), δ (CDCl₃—CD₃OD=10/1): 2.2–2.7 (m, 4H); 3.90, 4.27 (ABq, J=14.6 Hz, 2H); 4.902 (d-d, J₁=9 Hz, J₂=6.8 Hz, 1H); 7.057 (d, J=8.4 Hz, 1H); 7.28–3.37 (m, 2H)

(3)

10-Chloro-7-methyl-7,11b-dihydro-1H-pyrrolo[1,2-d][1,4]benzodiazepine-3,6(2H,5H)-dione (I c-1)

To a solution of 761 mg (3.036 mM) of the compound (I b-1) in 12 ml of DMF is added 146 mg (3.64 mM) of NaH (content 60%) under ice-cooling, and the mixture is stirred for 10 min. and further 10 min. at room temperature. The reaction mixture is added with 0.378 ml (6.072 mM) of CH₃I, and the mixture is stirred at room temperature for 50 min. and concentrated under reduced pressure. The resulting residue is mixed with ice-water, and the mixture is extracted with ethyl acetate. The ethyl acetate layer is washed with water, dried and concentrated. The resulting residue (848 mg) is recrystallized from CH₂Cl₂-Et₂O-n-hexane to give 708 mg (Yield: 88.1%) of the objective compound (I c-1) as needles.

Anal. Calcd. (%) for C₁₃H₁₃N₂O₂: C, 58.99; H, 4.95; N, 10.58; Cl, 13.39

Found (%): C, 59.04; H, 4.98; N, 10.65; Cl, 13.42

IR ν (CHCl₃): 1692, 1681(sh), 1601, 1573, 1489, 1446, 1410 cm⁻¹

NMR (200 MHz) δ (CDCl₃): 2.30–2.65 (m, 4H); 3.390 (s, 3H); 3.314, 4.590 (ABq, J=13.6 Hz, 2H) 4.747 (t, J=7.2 Hz, 1H); 7.247 (d, J=8.6 Hz, 1H); 7.343 (d, J=2.2 Hz, 1H); 7.451 (d-d, J₁=8.6 Hz, J₂=2.2 Hz, 1H)

EXAMPLE 11

10-Chloro-7-n-propyl-7,11b-dihydro-1H-pyrrolo[1,2-d][1,4]benzodiazepine-3,6(2H,5H)-dione (I c-2)

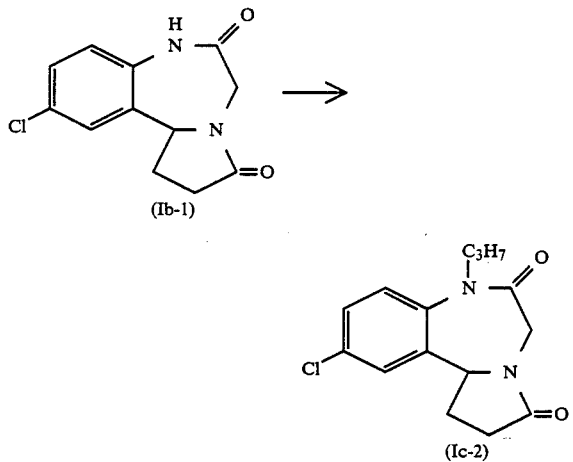

To a solution of 700 mg (2.792 mM) of the compound (I b-1) in 11 ml of DMF is added 134 mg (3.35 mM) of about 60% NaH under ice-cooling, and the mixture is stirred for 10 min. under ice-cooling. The reaction mixture is stirred at room temperature 10 min., mixed with 0.406 ml (4.467 mM) of n-propyl bromide, stirred at room temperature for 17 min. and 1 hour, and further mixed with 0.203 ml (2.234 mM) of n-propyl bromide. The mixture is stirred at room temperature for 55 min. and concentrated under reduced pressure to give a residue. The residue is mixed with water and extracted with ethy acetate. The ethyl acetate layer is washed with water, dried, and concentrated under reduced pressure to give a residue. The residue is chromatographed on a column of silica gel (70.1 g), eluting with toluene-acetone (4:1 v/v) to give 749 mg of the compound (I c-2). This is recrystallized from CH₂Cl₂-Et₂O-n-hexane to give 675 mg (Yield: 82.6%) of the objective compound (I c-2) melting at 125°–126° C. as colorless plates.

Anal. Calcd. (%) for C₁₅H₁₇ClN₂O₂: C, 61.54; H, 5.85; N, 9.57; Cl, 12.11

Found (%): C, 61.68; H, 5.94; N, 9.69; Cl, 11.88

IR,ν (CHCl₃): 1691, 1800, 1571, 1482, 1466, 1442, 1410 cm⁻¹

NMR (200 MHz), δ (CDCl₃): 0.872 (t, J=7.4 Hz, 3H); 1.49–1.60 (m, 2H); 2.30–2.60 (m, 4H); 3.264, 4.451 (ABq, J=13.2 Hz, 2H); 3.35–3.50 (m, 1H); 4.18–4.33 (m, 1H); 4.727 (t, J=7.4 Hz, 1H); 7.29 (d, J=8.2 Hz, 1H); 7.344 (d, J=2.4 Hz, 1H); 7.449 (dd, J₁=8.6 Hz, J₂=2.4 Hz, 1H)

EXAMPLE 12

7-Benzyl-10-chloro-7,11b-dihydro-1H-pyrrolo[1,2-d][1,4]benzo-diazepine-3,6(2H,5H)-dione (I c-3)

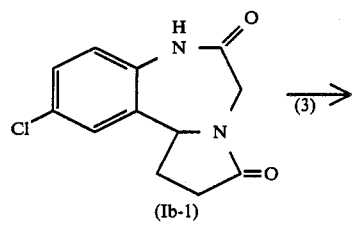

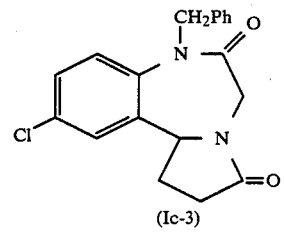

To a solution of 700 mg (2.792 mM) of the compound (I b-1) in 11 ml of DMF is added 134 mg (3.35 mM) of about 60% of NaH under ice-cooling, and the mixture is stirred for 10 min. under ice-cooling and stirred for 20 min. at room temperature. The solution is added with 0.364 ml (3.071 mM) of benzyl bromide, stirred at room temperature for 1.5 hr. and concentrated under reduced pressure. The resulting residue is mixed with water and extracted with ethyl acetate. The ethyl acetate layer is washed with water, dried, and concentrated under reduced pressure. The resulting residue is chromatographed on a column of silica gel (70.4 g), eluting with toluene-acetone (4/1 v/v) to give 836 mg of the compound (I c-3). This is recrystallized from CH₂Cl₂-Et₂O-n-hexane to give 760 mg (Yield: 79.9%) of the objective compound (I c-3) melting at 161.5°–162.5° C. as colorless needles.

Anal Calcd. (%) for C₁₉H₁₇ClN₂O₂: C, 66.96; H, 5.30; N, 8.22; Cl, 10.40

Found (%): C, 66.90; H, 5.18; N, 8.27; Cl, 10.67

IRν (CHCl₃): 1690, 1602, 1587, 1571, 1485, 1455, 1445, 1410 cm⁻¹

NMR (200 MHz) δ (CDCl₃): 2.20–2.60 (m, 4H); 3.350, 4.602 (ABq, J=13.2 Hz, 2H); 4.433 (d-d, J₁=8.2 Hz, J₂=6.8 Hz, 1H); 4.544, 5.299 (ABq, J=14.8 Hz, 2H); 7.15–7.43 (m, 8H)

EXAMPLE 13

10-Fluoro-7-n-propyl-7,11b-dihydro-1H-pyrrolo[1,2-d][1,4]benzodiazepine-3,6(2H,5H)-dione (I c-4)

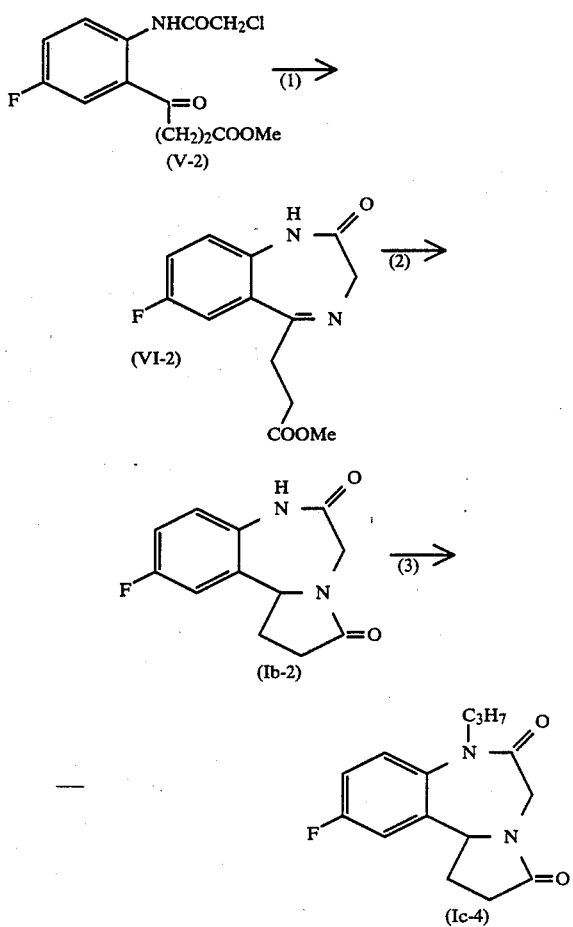

(1)
7-Fluoro-5-(2-methoxycarbonylethyl)-2H-[1,4]benzodiazepin-2-one (VI-2)

To a solution of 9.192 mg (30.467 mM) of the compound (V-2) in 460 ml of $CH_3CN$ are added 5.48 g (36.560 mM) of NaI and 23.00 g (239 mM) of $(NH_4)_2CO_3$, and the mixture is allowed to stand at room temperature for 63.5 hr. and concentrated. The resulting residue is poured into aqueous $Na_2S_2O_3$, and the mixture is extracted with $CH_2Cl_2$. The $CH_2Cl_2$ layer is washed with saturated brine, dried, and concentrated. The resulting residue is chromatographed on a column of silica gel (230 g), eluting with toluene-acetone (4:1 v/v) to give 6.10 g of the objective compound (VI-2). This is recrystallized from $CH_2Cl_2$-$Et_2O$-n-hexane to give 5.702 g (Yield: 70.8%) of the compound (VI-2) melting at 137°–138° C. as pale yellowish green needles.

Anal. Calcd. (%) for $C_{13}H_{13}FN_2O_3$: C, 59.09; H, 4.96; N, 10.60; F, 7.19

Found (%): C, 59.23; H, 4.95; N, 10.65; F, 7.14

IR $\nu$ (CHCl$_3$): 3400, 1732, 1687, 1585, 1493, 1457, 1438, 1400 cm$^{-1}$

NMR (200 MHz) δ (CDCl$_3$): 2.739 (t, J=6.6 Hz, 2H); 3.020 (t, J=6.6 Hz, 2H); 3.673 (s, 3H); 4.125 (s, 2H); 7.02 (d-d, J$_1$=9 Hz, J$_2$=5 Hz, 1H); 7.192 (d-d-d, J$_1$=9 Hz, J$_2$=7.4 Hz, J$_3$=2.8 Hz, 1H); 7.349 (d-d, J$_1$=9 Hz, J$_2$=2.8 Hz, 1H); 9.177 (br, 1H)

(2)
10-Fluoro-7,11b-dihydro-1H-pyrrolo[1,2-d][1,4]benzodiazepine-3,6(2H,5H)-dione (I b-2)

To a solution of 5.651 g (21.385 mM) of the compound (VI-2) in 120 ml of acetic acid is added 2.83 g (42.77 mM) of NaBH$_3$CN, and the mixture is stirred at room temperature for 1.5 hr. and concentrated under reduced pressure. The resulting residue is mixed with ice-water and the mixture is basified with Na$_2$CO$_3$ and extracted with CH$_2$Cl$_2$. The CH$_2$Cl$_2$ layer is washed with saturated aqueous brine, dried, and concentrated. The resulting blue foamy material is dissolved in 28 ml of acetic acid and the solution is heated at 65° C. for 1 hour and concentrated. The resulting residue is washed with Et$_2$O for crystallization and recrystallized from CH$_2$Cl$_2$-Et$_2$O to give 3.830 g (Yield: 76.5%) of the objective compound (I b-2) melting at 185°–186° C. as prisms.

Anal. Calcd. (%) for $C_{12}H_{11}FN_2O_2$: C, 61.53; H, 4.73; N, 11.96; F, 8.11

Found (%): C, 61.47; H, 4.82; N, 11.98; F, 7.82

IR $\nu$ (CHCl$_3$): 3390, 3210, 1697, 1619, 1599, 1499, 1457, 1412 cm$^{-1}$

NMR (200 MHz) δ (CDCl$_3$): 2.2–2.6 (m, 4H); 3.88, 4.33 (ABq, J=14.4 Hz, 2H); 4.903 (d-d, J$_1$=8.8 Hz, J$_2$=6.4 Hz, 1H); 7.00–7.15 (m, 3H); 8.901 (br, 1H).

(3)
10-Fluoro-7-n-propyl-7,11b-dihydro-1H-pyrrolo[1,2-d][1,4]benzodiazepine-3,6(2H,5H)-dione (I c-4)

To a solution of 500 mg (2.135 mM) of the compound (I b-2) in 9 ml of DMF is added 103 mg (2.56 mM) of about 60% NaH under ice-cooling, and the mixture is stirred for 10 min. under ice-cooling and for 10 min. at room temperature. The mixture is added with 0.466 ml (5.12 mM) of n-propyl bromide, stirred at room temperature for 55 min., mixed again with 0.200 ml (2.20 mM) of n-propyl bromide, stirred at room temperature for 30 min. and concentrated under reduced pressure. The resulting residue is mixed with water and extracted with ethyl acetate. The ethyl acetate layer is washed with water, dried, and concentrated under reduced pressure. The resulting residue is chromatographed on a column of silica gel (60.0 g), eluting with CHCl$_3$—MeOH (100:1 v/v) to give 532 mg of the compound (I c-4). This is recrystallized from CH$_2$Cl$_2$-Et$_2$O-n-hexane to give 444 mg (Yield: 75.3%) of the objective compound (I c-4) melting at 121.5°–122.5° C. as colorless plates.

Anal. Calcd. (%) for $C_{15}H_{17}FN_2O_2$: C, 65.20; H, 6.20; N, 10.14; F, 6.88

Found (%): C, 65.31; H, 6.40; N, 10.16; F, 6.99

IR $\nu$ (CHCl$_3$): 1691, 1675(sh), 1594, 1467, 1437, 1410, 1400(sh) cm$^{-1}$

NMR (200 MHz) δ (CDCl$_3$): 0.883 (t, J=7.4 Hz, 3H); 1.50–1.64 (m, 2H); 2.31–2.62 (m, 4H); 3.267, 4.540 (ABq, J=13.2 Hz, 2H); 3.35–3.50 (m, 1H); 4.20–4.35 (m, 1H); 4.751 (t, J=7.6 Hz, 1H); 7.05–7.22 (m, 2H); 7.343 (d-d, J$_1$=8.8 Hz, J$_2$=5 Hz, 1H)

EXAMPLE 14

7-Benzyl-10-fluoro-7,11b-dihydro-1H-pyrrolo[1,2-d][1,4]benzodiazepine-3,6(2H,5H)-dione (I c-5)

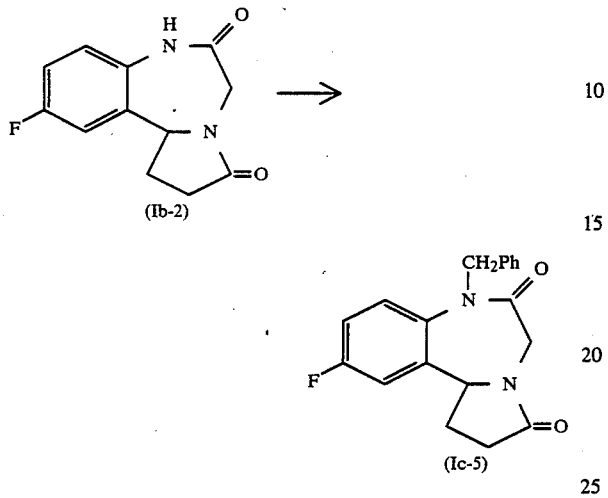

To a solution of 500 mg (2.135 mM) of the compound (I b-2) in 9 ml of DMF is added 103 mg of about 60% NaH under ice-cooling, and the mixture is stirred for 10 min. under ice-cooling and further for 15 min. at room temperature. The mixture is mixed with 0.278 ml (2.35 mM) of benzyl bromide, stirred at room temperature for 1 hour and concentrated under reduced pressure. The resulting residue is mixed with water and extracted with ethyl acetate. The ethyl acetate layer is washed with water, dried and concentrated under reduced pressure. The resulting residue in 709 mg is chromatographed on a column of silica gel (62.1 g), eluting with toluene-acetone (4:1 v/v) to give 693 mg of the compound (I c-5). This is recrystallized from $CH_2Cl_2$-$Et_2O$-n-hexane to give 552 mg (Yield: 79.7%) of the objective compound (I c-5) melting at 150.05°–151.0° C. as colorless plates.

Anal. Calcd. (%) for $C_{19}H_{17}FN_2O_2$: C, 70.36; H, 5.28; N, 8.64; F, 5.86

Found (%): C, 70.45; H, 5.38; N, 8.55; F, 5.68

IR $\nu$ (CHCl$_3$): 3690, 1691, 1597, 1497, 1456, 1439, 1413, 1396 cm$^{-1}$

NMR (200 MHz) $\delta$ (CDCl$_3$): 2.18–2.60 (m, 4H); 3.347, 4.595 (ABq, J=13.2 Hz, 2H); 4.433 (t, J=7.5 Hz, 1H); 4.793, 5.290 (ABq, J=14.6 Hz, 2H); 6.96–7.37 (m, 8H)

EXAMPLE 15

7-n-Propyl-7,11b-dihydro-1H-pyrrolo[1,2-d][1,4]benzodiazepine-3,6(2H,5H)-dione (I c-6)

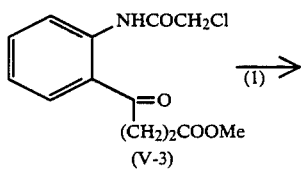

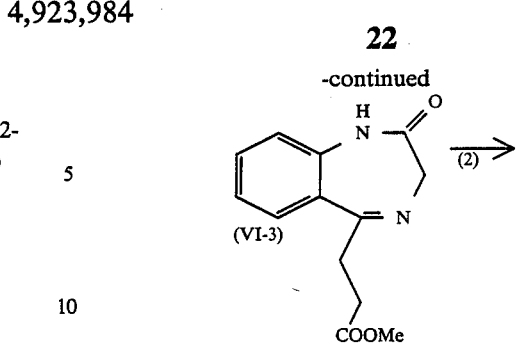

(1) To a solution of 4.969 g (17.514 mM) of the compound (V-3) in 264 ml of CH$_3$CN are added 3.15 g (21.014 mM) of NaI and 13.22 g (137.576 mM) of (NH$_4$)$_2$CO$_3$, and the mixture is allowed to stand at room temperature for 63 hr. and concentrated under reduced pressure. The resulting residue is poured into aqueous Na$_2$S$_2$O$_3$ and the solution is extracted with CH$_2$Cl$_2$. The CH$_2$Cl$_2$ layer is washed with saturated brine, dried and concentrated. The residue is chromatographed on a column of silica gel, eluting with toluene-acetone (4:1 v/v) to give 2.83 g of the objective compound (VI-3). This is recrystallized from CH$_2$Cl$_2$-Et$_2$O-n-hexane to give 2.586 g (Yield: 60.0%) of the compound (VI-3) melting at 145.5°–146.5° C. as blue pillars.

Anal. Calcd. (%) for $C_{13}H_{14}N_2O_3$: C, 63.40; H, 5.73; N, 11.38

Found (%): C, 63.58; H, 5.72; N, 11.49

IR $\nu$ (CHCl$_3$): 3692, 3400, 1733, 1688, 1608, 1580, 1496, 1482, 1469, 1439, 1410 cm$^{-1}$

NMR (200 MHz) $\delta$ (CDCl$_3$): 2.724 (t, J=7 Hz, 2H); 3.067 (t, J=7 Hz, 2H); 3.667 (s, 3H); 4.122 (s, 2H); 7.105 (d-d, J$_1$=8 Hz, J$_2$=1.2 Hz, 1H); 7.229 (t-d, J$_1$=8 Hz, J$_2$=1.2 Hz, 1H); 7.466 (t-d, J$_1$=8 Hz, J$_2$=1.2 Hz, 1H); 7.650 (d-d, J$_1$=8 Hz, J$_2$=1.6 Hz, 1H); 9.117 (br, 1H)

(2) To a solution of 2.799 g (11.366 mM) of the compound (VI-3) in 64 ml of acetic acid is added 1.504 g (22.732 mM) of NaBH$_3$CN under ice-cooling, and the mixture is stirred at room temperature for 1.5 hours and concentrated under reduced pressure. The resulting residue is mixed with ice-water, and the solution is basified with Na$_2$CO$_3$ and extracted with CH$_2$Cl$_2$. The CH$_2$Cl$_2$ layer is washed with saturated brine, dried and concentrated to give a blue foamy material. This material in 2.834 g is dissolved in 26 ml of acetic acid, and the solution is stirred at room temperature for 40 min. and 16 hr. and concentrated under reduced pressure. The resulting residue is washed with Et$_2$O and recrystallized from CH₂Cl₂-Et₂O to give 2.20 g (Yield: 89.5%) of the compound (I b-3) melting at 203.5°-205.0° C. as prisms.

Anal. Calcd. (%) for $C_{12}H_{12}N_2O_2$: C, 66.65; H, 5.59; N, 12.96

Found (%): C, 66.60; H, 5.57; N, 13.00

IR $\nu$ (CHCl₃): 3190, 3120, 3075, 1702, 1668, 1608, 1586, 1498, 1485, 1452, 1441, 1389 cm⁻¹

NMR (200 MHz) δ (CDCl₃): 2.25–2.65 (m, 4H); 3.945, 4.314 (ABq, J=14.4 Hz, 2H); 4.937 (d-d, J₁=8.8 Hz, J₂=6.6 Hz, 1H); 7.109 (d-d, J₁=7 Hz, J₂=1 Hz, 1H); 7.20–7.40 (m, 3H); 8.713 (br, 1H)

(3) To a solution of 500 mg (2.312 mM) of the compound (I b-3) in 9 ml of DMF is added 111 mg (2.77 mM) of about 60% NaH under ice-cooling, and the mixture is stirred under ice-cooling for 10 min., and at room temperature for 12 min. The mixture is mixed with 0.504 ml (5.548 mM) of n-propyl bromide, and stirred at room temperature for 60 min. and concentrated under reduced pressure. The resulting residue is mixed with water and extracted with ethyl acetate. The ethyl acetate layer is washed with water, dried and concentrated under reduced pressure. The residue in 599 mg is chromatographed on a column of silica gel (91.4 g), eluting with toluene-acetone (4:1-3:1 v/v) to give 540 mg of the compound (I c-6). This is recrystallized from a mixture of CH₂Cl₂-Et₂O-n-hexane to give 485 mg (Yield: 81.2%) of the objective compound (I c-6) melting at 157.5°-158.5° C. as colorless prisms.

Anal Calcd. (%) for $C_{15}H_{18}N_2O_2$: C, 69.74; H, 7.02; N, 10.84

Found (%): C, 69.93; H, 7.06; N, 10.86

IR $\nu$ (CHCl₃): 3685, 1688, 1603, 1582, 1490, 1460, 1429, 1413, 1398 cm⁻¹

NMR (200 MHz) δ (CDCl₃): 0.875 (t, J=7.0 Hz, 3H); 1.50–1.65 (m, 2H); 2.34–2.60 (m, 4H); 3.271, 4.528 (ABq, J=13.2 Hz, 2H); 3.40–3.55 (m, 1H); 4.19–4.35 (m, 1H); 4.766 (d-d, J₁=8 Hz, J₂=6 Hz, 1H); 7.32–7.53 (m, 4H)

EXAMPLE 16

7-n-Propyl-7,11b-dihydro-1H-pyrrolo[1,2-d][1,4]benzodiazepine-3,6-(2H,5H)-dione (I c-7)

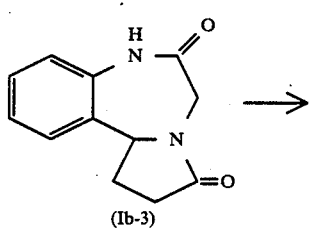

To a solution of 500 mg (2.312 mM) of the compound (I b-3) in 9 ml of DMF is added 111 mg (2.77 mM) of about 60% NaH under ice-cooling, and the mixture is stirred for 10 minutes under ice-cooling, stirred at room temperature for 15 minutes, mixed with 0.301 ml (2.54 mM) of benzyl bromide, and stirred at room temperature for 55 minutes. The mixture is concentrated under reduced pressure to give a residue, which is mixed with water and extracted with ethyl acetate. The ethyl acetate layer is washed with water, dried, and concentrated under reduced pressure. The residue 817 mg is chromatographed on a column of silica gel (93.4 g), eluting with toluene-acetone (4:1 v/v) to give 639 mg of the compound (I c-7). This is recrystallized from CH₂Cl₂-Et₂O-n-hexane to give 601 mg (Yield: 84.8%) of colorless prisms.

Anal Calcd. (%) for $C_{19}H_{18}N_2O_2$: C, 74.49; H, 5.92; N, 9.14

Found (%): C, 74.70; H, 5.93; N, 9.11

IR $\nu$ (CHCl₃): 1688, 1606, 1584, 1496, 1462, 1458, 1446, 1430, 1416, 1397 cm⁻¹

NMR (200 MHz) δ (CDCl₃): 2.17–2.58 (m, 4H); 3.363, 4.590 (ABq, J=13.2 Hz, 2H); 4.482 (d-d, J₁=8.6 Hz, J₂=6.6 Hz, 1H); 4.860, 5.293 (ABq, J=14.6 Hz, 2H); 7.16–7.48 (m, 9H)

EXAMPLE 17

7-Methyl-7,11b-dihydro-1H-pyrrolo[1,2-d][1,4]benzodiazepine-3,6-(2H,5H)-dione (I c-8)

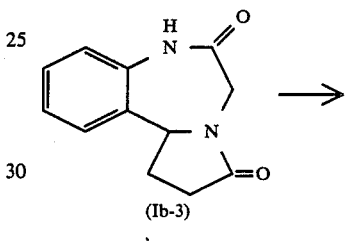

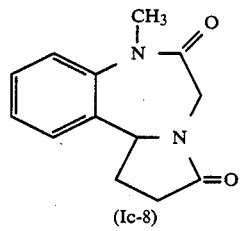

To a solution of 510 mg (2.358 mM) of the compound (I b-3) in 10 ml of DMF is added 113 mg (1.2 mM) of about 60% NaH under ice-cooling, and the mixture is stirred for 15 minutes under ice-cooling, stirred at room temperature for 10 minutes, mixed with 0.294 ml (4.716 mM) of methyl iodide, stirred at 0° C. for 10 min. and further at room temperature for 1 hour. The reaction mixture is concentrated under reduced pressure to give a residue, which is poured into water. The solution is extracted with ethyl acetate, and the ethyl acetate layer is washed with water, saturated NaCl, and water in order. The solution is dried over magnesium sulfate and concentrated under reduced pressure to give 371 mg of colorless crystals. The aqueous layer was similarly operated to give 173 mg of colorless crystals. Both crystals are combined in total 544 mg and recrystallized from CH₂Cl₂-Et₂O to give 446 mg (Yield: 82.1%) of the objective compound (I c-8) as colorless crystals melting at 189.0°-190.5° C.

Anal Calcd. (%) for $C_{13}H_{14}N_2O_2$: C, 67.81; H, 6.13; N, 12.17

Found (%): C, 67.85; H, 6.14; N, 12.09

IR $\nu$ (CHCl₃): 1690, 1605, 1586, 1494, 1459, 1442, 1412 cm⁻¹

IR $\nu$ (Nujol): 3075, 1693, 1670, 1602, 1498, 1462, 1441, 1414 cm⁻¹

NMR (200 MHz) δ (CDCl₃): 2.30–2.65 (m, 4H); 3.420 (s, 3H); 3.325, 4.584 (ABq, J=13.4 Hz, 2H); 4.790 (d-d, J₁=9 Hz, J₂=6 Hz, 1H); 7.27–7.53 (m, 4H)

REFERENCE EXAMPLE 1

N-(2-Methoxycarbonylphenyl)-2-oxopyrrolidine-5-carboxyamide (II-1)

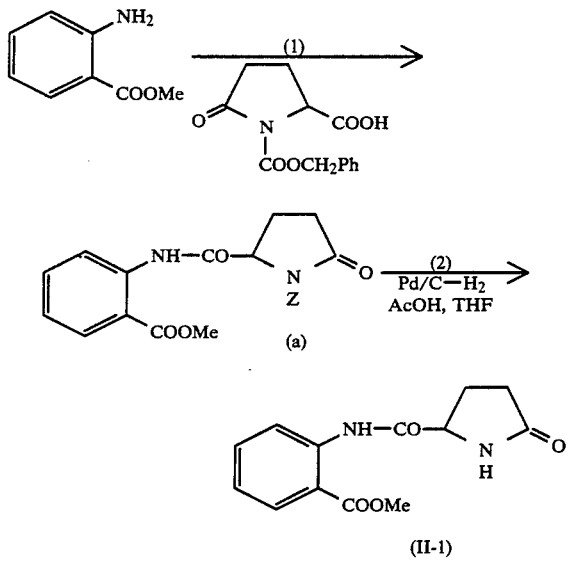

(1)
N-(2-Methoxycarbonyl)-1-benzyloxycarbonyl-2-oxo-pyrrolidine-5-carboxyamide (a)

Method A

To a solution of 1.217 g (8.051 mM) of 2-methoxycarbonylaniline and 2.12 g (8.051 mM) of L-benzyloxycarbonylpyroglutamic acid in 25 ml of THF are added 326 mg (2.41 mM) of HOBT and 1.988 g (9.66 mM) of DCC, and the mixture is allowed to stand at room temperature for 66 hr. The reaction mixture is filtered off to remove the precipitate and concentrated. The residue is dissolved in ethyl acetate, and the organic layer is washed with d-HCl, water, aqueous NaHCO₃ in order, dried and concentrated. The residue is chromatographed on a column of silica gel (116.1 g), eluting with benzene-acetone (9:1 v/v) to give 2.543 g (Yield: 79.7%) of the compound (a). Recrystallization from Et₂O-acetone gives prisms melting at 169°–170° C.

Anal. Calcd. (%) for C₂₁H₂₀N₂O₆: C, 63.63; H, 5.09; N, 7.07

Found (%): C, 63.60; H, 5.17; N, 7.07

[α]_D^{21.0} −18.9±0.6 (c=1.006, CHCl₃)

IR ν (CHCl₃): 3270, 1758, 1709, 1700, 1688, 1609, 1592, 1532, 1496, 1453, 1439, 1419 cm⁻¹

NMR (90 MHz) δ (CDCl₃): 2.17–2.9 (m, 4H); 3.86 (s, 3H); 4.60–4.75 (m, 1H); 5.17, 5.80 (ABq, 2H); 7.0–7.7 (m, 7H); 8.30 (d-d, J₁=9 Hz, J₂=2 Hz, 1H); 8.65 (d, J=9 Hz, 1H)

Method B

To a solution of 14.191 g (93.878 mM) of 2-methoxycarbonylaniline and 24.713 g (93.878 mM) of L-benzyloxycarbonylpyrogultamic acid in 356 ml of THF is added a solution of 27.858 g (112.654 mM) of EEDQ in 356 ml of THF, and the mixture is allowed to stand at room temperature for 24 hours. The resulting crystals are collected by filtration and washed with THF to give 23.76 g of crystals melting at 168°–169° C. The filtrate is washed with d-HCl, water, and NaHCO₃ in order, dried and concentrated. The resulting residue is crystallized from Et₂O to give 2.026 g (Yield: 69.3%) of crude product. The product is recrystallized from acetone-Et₂O to give 24.17 g (Yield: 63.7%) of the objective compound (a) melting at 168°–169° C.

(2) To a solution of 3.06 g (7.719 mM) of the compound (a) in 30 ml of THF are added 15 ml of acetic acid and 4 ml of water, and the mixture is hydrogenated in the presence of 356 mg of 10% Pd-C at room temperature. The reaction mixture is concentrated after the catalyst is filtered off. The residue is dissolved in ethyl acetate, and the organic layer is washed with saturated brine, dried and concentrated. The resulting residue is crystallized from Et₂O to give 1.794 g (Yield: 88.6%) of the objective compound (II-1) melting at 131°–132° C. as colorless crystals.

Anal. Calcd. (%) for C₁₃H₁₄N₂O₄: C, 59.54; H, 5.38; N, 10.68

Found (%): C, 59.51; H, 5.43; N, 10.64

[α]_D^{21.5} −34.8°±0.8° (c=1.000, CHCl₃)

IR ν (CHCl₃): 3435, 3270, 1699, 1609, 1592, 1530, 1452, 1438, 1438, 1408 cm⁻¹

NMR (90 MHz) δ (CDCl₃): 2.15–2.75 (m, 4H); 3.87 (s, 3H); 4.20–4.4 (m, 1H); 6.97–7.60 (m, 3H); 7.95 (d-d, J₁=9 Hz, J₂=2 Hz, 1H); 8.65 (d, J=9 Hz, 1H)

REFERENCE EXAMPLE 2

N-(2-Methoxycarbonylphenyl)-N-methyl-2-oxopyrrolidine-5-carboxyamide (II-2)

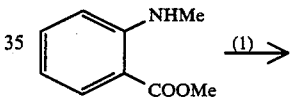

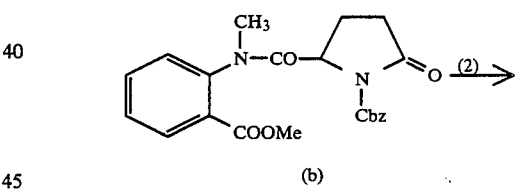

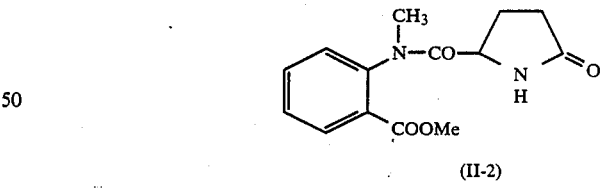

(1) To a solution of 2.25 g (13.621 mM) of methyl N-methylanthranilate and 3.586 g (13.621 mM) of L-benzyloxycarbonyl-pyroglutamic acid in 45 ml of THF are added 1.484 ml (20.432 mM) of SOCl₂ and 4.407 ml (54.484 mM) of pyridine, and the mixture is refluxed for 21 hours under heating and concentrated to give a residue. The residue is dissolved in CHCl₃. The solution is washed with d-HCl, water, and aqueous NaHCO₃ in order, dried and concentrated. The residue is chromatographed on a column of silica gel (296.8 g), eluting with benzene-acetone (7:1-3:1 v/v) to give 4.293 g (Yield: 76.8%) of the compound (b). This is recrystallized from Et₂O-acetone to give 3.282 g (Yield: 53.9%) of the compound (b) melting at 116°–118° C. as prisms.

Anal. Calcd. (%) for $C_{22}H_{22}N_2O_6$: C, 64.38; H, 5.40; N, 6.83

Found (%): C, 64.25; H, 5.45; N, 6.79

$[\alpha]_D^{22.0}$ +123.8°+1.6° (c=1.011, $CHCl_3$)

IR $\nu$ ($CHCl_3$): 1797, 1757, 1727, 1670, 1601, 1579, 1492, 1454, 1436 $cm^{-1}$

NMR (90 MHz) $\delta$ ($CDCl_3$): 1.4–2.9 (m, 4H); 3.20 (s, 3H); 3.90 (s, 3H); 4.45 (d-d, $J_1$=9 Hz, $J_2$=3 Hz, 1H); 5.27, 5.30 (ABq, J=15 Hz, 2H); 7.0–8.1 (m, 9H)

(2) A solution of 3.784 g (9.22 mM) of the compound (b) in 40 ml of methanol and 5 ml of water is hydrogenated in the presence of 423 mg of 10% Pd/C at room temperature. The reaction mixture is concentrated under reduced pressure after the catalyst is filtered off. The resulting residue is mixed with $CHCl_3$ and the solution is washed with saturated brine, dried and concentrated to give 2.482 g of crude product. This is recrystallized from $Et_2O$-MeOH to give the objective compound (II-2) melting at 143°–144° C. as colorless prisms.

$[\alpha]^{23.0}$+1.0°±0.4° (c=1.015, $CHCl_3$)

NMR (90 MHz) $\delta$ ($CDCl_3$-$d_4$MeOH): 1.8–2.5 (m, 4H); 3.20 (s, 3H); 3.90 (s, 3H); 3.97–4.15 (m, 1H); 7.2–8.2 (m, 4H)

REFERENCE EXAMPLE 3

N-Benzyl isatoic anhydride (III-1)

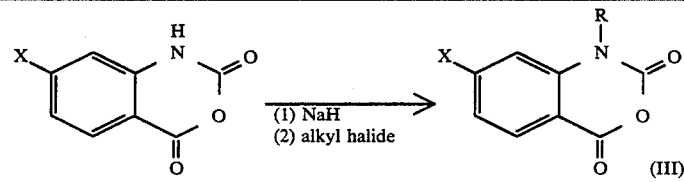

(III-1)

To a solution of 5.00 g (30.65 mM) of N-isatoic anhydride in 62 ml of DMA is added 1.471 g (36.78 mM) of about 60% NaH, and the mixture is stirred at room temperature for 35 min.*[1] The reaction mixture is mixed with 4.0 ml (33.715 mM) of benzyl bromide, stirred at room temperature for 15 hr.*[2] and concentrated under reduced pressure. The residue is poured into ice water and the resulting product is filtered, washed with water, and dried. Recrystallization from $CH_2Cl_2$-$Et_2O$ gives 6.274 g (Yield: 80.8%) of the objective compound (III-1) melting at 143°–145° C. as needles.

*[1]: reaction condition 1 (See Table 1)
*[2]: reaction condition 1 (See Table 1)

NMR (90 MHz) $\delta$ ($CDCl_3$): 5.28 (s, H); 7.07–8.20 (m, 9H)

REFERENCE EXAMPLES 4–8

The reaction is performed as described in Reference Example 3, whereby the objective compounds are obtained.

The physical properties of the objective compounds are shown in Table 1 and 2.

TABLE 1

| Ref. Ex. No. | Starting Material X | g (mM) | DMA (ml) | 60% NaH g (mM) | Reaction Conditions (1) Time (min) | Temp. (°C.) | Halide ml (mM) | Reaction Conditions (2) Time (min) | Temp. (°C.) | Recrystallized from | Product Compd. No. R | Yield (g) | (%) |
|---|---|---|---|---|---|---|---|---|---|---|---|---|---|
| 4 | H | 5.09 (30.65) | 62 | 1.471 (36.78) | 60 | r.t. | PhBr 4.47(49.4) | 42 | r.t. | $CH_2Cl_2$—n.hexane | III-2 Pr | 3.137 | 49.9 |
| 5 | OMe | 4.00 (20.71) | 42 | 0.994 (24.85) | 40 | r.t. | $CH_3I$ 2.6(41.41) | 1.25 | r.t. | $CH_2Cl_2$—$Et_2O$ | III-3 Me | 2.166 | 50.5 |
| 6 | OMe | 4.00 (20.71) | 42 | 0.994 (24.85) | 40 | r.t. | $PhCH_2Br$ 2.7(22.78) | 2 | r.t. | acetone-$Et_2O$ | III-4 $CH_2Ph$ | 4.799 | 81.8 |
| 7 | F | 4.019 (22.19) | 45 | 1.065 (26.627) | 40 | r.t. | $CH_3I$ 2.76(44.38) | 2 | r.t. | $CH_2Cl_2$—$Et_2O$ | III-5 Me | 3.855 | 89.1 |
| 8 | F | 8.586 (47.41) | 96 | 2.275 (56.886) | —40 | r.t. | $PhCH_2Br$ 6.18(52.15) | 17 | r.t. | $CH_2Cl_2$—$Et_2O$ | III-6 $CH_2Ph$ | 11.323 | 88.1 | r.t.: room temperature

TABLE 2

| Compd. No. | m.p. °C. | Anal. Calcd. (%) Found (%) | IR ($cm^{-1}$) | NMR |
|---|---|---|---|---|
| III-2 | 94–98 | — | — | ($CDCl_3$) 1.04 (t, J=7Hz, 3H); 1.60–2.0 (m, 2H); 4.02 (d-d, $J_1$=$J_2$=7Hz, 2H); 7.1–8.2 (m, 4H) |
| III-3 | 200–201 | — | — | ($d_6$-DMSO) 3.45 (s, 3H); 3.92 (s, 3H); 6.81 (d, J=1Hz; 1H); 6.89 (d-d, $J_1$=9Hz, $J_2$=1Hz, |

TABLE 2-continued

| Compd. No. | m.p. °C. | Anal. Calcd. (%) Found (%) | IR (cm$^{-1}$) | NMR |
|---|---|---|---|---|
| III-4 | 167–168 | — | — | 1H); 7.90 (d, J=9Hz, 1H) (d$_6$-DMSO) 3.78 (s, 3H); 5.30 (s, 2H); 6.69 (d, J=2Hz, 1H); 6.85 (d-d, J$_1$=9Hz, J$_2$=2Hz, 1H); 7.2–7.4 (m, 5H); 7.95 (d, J=9Hz, 1H) |
| III-5 | 161–162 | C$_9$H$_6$NO$_3$F C, 55.39 (55.30) H, 3.10 (3.28) N, 7.18 (7.23) F, 9.74 (9.76) | (Nujol) 3148, 3107, 1719, 1781, 1756, 1737, 1623, 1602, 1514, 1475, 1466 (sh) | (d$_6$-DMSO) 3.46 (s, 3H); 7.06–7.50 (m, 2H); 8.10 (d-d, J$_1$=10Hz, J$_2$=7Hz, 1H) |
| III-6 | 143–144.5 | C$_{15}$H$_{10}$NO$_3$F C, 66.42 (66.44) H, 3.72 (3.82) N, 5.16 (5.25) F, 7.00 (6.93) | (CHCl$_3$) 1739, 1622, 1602, 1511, 1500, 1469, 1458, | (CDCl$_3$) 5.24 (s, 2H); 6.70–7.05 (m, 2H); 7.33 (brs, 5H); 8.16 (d-d, J$_1$=10Hz, J$_2$=7Hz, 1H) |

REFERENCE EXAMPLE 9

Methyl 4-(2-chloroacetylamino-5-chlorophenyl)-4-oxobutylate (V-1)

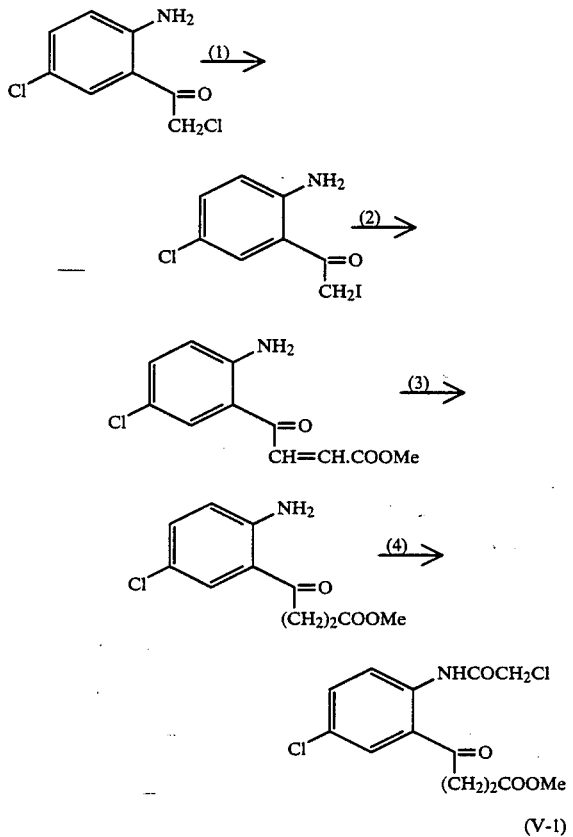

(1) To a solution of 11.208 g (54.93 mM) of 2'-amino-2,5'-di-chloroacetophenone in 281 ml of CH$_3$CN is added 24.7 g (165 mM) of NaI, and the mixture is stirred at room temperature for 2.5 hr. and concentrated under reduced pressure. The residue is dissolved in ethyl acetate, washed with aqueous Na$_2$S$_2$O$_3$, and brine in order, dried and concentrated to give 16.1 g (Yield: 99.2%) of 2'-amino-5'-chloro-2-iodoacetophenone as crystals.

NMR (90 MHz) δ (CDCl$_3$): 4.28 (s, 2H); 6.60 (d, J=9 Hz, 1H); 7.23 (d-d, J$_1$=9 Hz, J$_2$=2 Hz, 1H); 7.62 (d, J=2 Hz, 1H); 6.30 (br, 2H, disappeared by adding CD$_3$OD)

(2) To a solution of 8.494 g (28.7 mM) of 2'-amino-5'-chloro-2-iodoacetophenone in 142 ml of benzene is added 19.233 g (57.488 mM) of triphenylphosphine carbomethoxymethylene, and the mixture is stirred at room temperature for 18 hr. After removal of precipitates, the filtrate is chromatographed on a column of silica gel (800 g), eluting with toluene-ethyl acetate (49:1–30:1 v/v) to give 5.70 g (Yield: 82.7%) of crude product. This is recrystallized from Et$_2$O-n-hexane to give 5.148 g (Yield: 74.7%) of methyl 4-(2-amino-5-chlorophenyl)-4-oxo-2-butenoate melting at 111°–112° C. as orange needles.

Anal. Calcd. (%) for C$_{11}$H$_{10}$ClNO$_3$: C, 55.13; H, 4.21; N, 5.84; Cl, 14.79

Found (%): C, 55.04; H, 4.28; N, 5.90; Cl, 14.74

IR ν (CHCl$_3$): 3695, 3610, 3505, 3350, 1726, 1652, 1617, 1579, 1539, 1471, 1437, 1410 cm$^{-1}$

NMR (90 MHz) δ (CDCl$_3$): 3.38 (s, 3H); 6.78, 7.88 (ABq, J=15 Hz, 2H); 6.62 (d, J=9 Hz, 1H); 7.23 (d-d, J$_1$=9 Hz, J$_2$=2 Hz, 1H); 7.67 (d, J=2 Hz, 1H)

(3) A solution of 4.435 g (18.506 mM) of methyl 4-(2-amino-5-chlorophenyl)-4-oxo-2-butenoate in 118 ml of dioxane is hydrogenated in the presence of 887 mg of 10% Pd-C under ordinaly pressure at room temperature. The mixture is concentrated after removal of the catalyst. The resulting residue is chromatographed on a column of silica gel (220 g), eluting with toluene-ethyl acetate (49:1–30:1 v/v) to give 3.877 g (Yield: 86.7%) of methyl 4-(2-amino-5-chlorophenyl)-4-oxobutyrate. This is recrystallized from CH$_2$Cl$_2$-Et$_2$O-n-hexane to give light yellow scaly prisms melting at 78°–79° C.

IR ν (CHCl$_3$): 3495, 3351, 1732, 1655, 1612, 1579, 1540, 1476, 1438, 1413 cm$^{-1}$

NMR (90 MHz) δ (CDCl$_3$): 2.69 (t, J=7 Hz, 2H); 3.25 (t, J=7 Hz, 2H); 3.71 (s, 3H); 6.00 (br, disappeared by adding CD$_3$OD, 2H); 6.57 (d, J=9 Hz, 1H); 7.18 (d-d, J$_1$=9 Hz, J$_2$=2 Hz, 1H); 7.68 (d, J=2 Hz, 1H)

(4) To a solution of 5.286 g (21.872 mM) of methyl 4-(2-amino-5-chlorophenyl)-4-oxobutyrate in 53 ml of CH$_2$Cl$_2$ is added 2.09 ml (26.246 mM) of chloroacetyl chloride, and the mixture is stirred at room temperature for 15 minutes and 1 hour. The reaction mixture is poured into aqueous NaHCO$_3$ under ice-cooling, and the organic layer is washed with water, dried and concentrated. The crystalline residue (6.937 g) is recrystallized from CH$_2$Cl$_2$-Et$_2$O-n-hexane to give 6.474 g (Yield: 93%) of the compound (V-1) melting at 108°–109° C. as light yellow crystals.

IR ν (CHCl₃): 3200 (br), 1732, 1681, 1665, 1600, 1578, 1503, 1438, 1402 cm⁻¹

NMR (90 MHz), δ (CDCl₃): 2.77 (t, J=7 Hz, 2H); 3.36 (t, J=7 Hz, 2H); 3.72 (s, 3H); 4.17 (s, 2H); 7.55 (d-d, J₁=9 Hz, J₂=2 Hz, 1H); 7.95 (d, J=2 Hz, 1H); 8.73 (d, J=9 Hz, 1H)

REFERENCE EXAMPLE 10

Methyl 4-(2-Chloroacetylamino-5-fluorophenyl)-4-oxobutyrate (V-2)

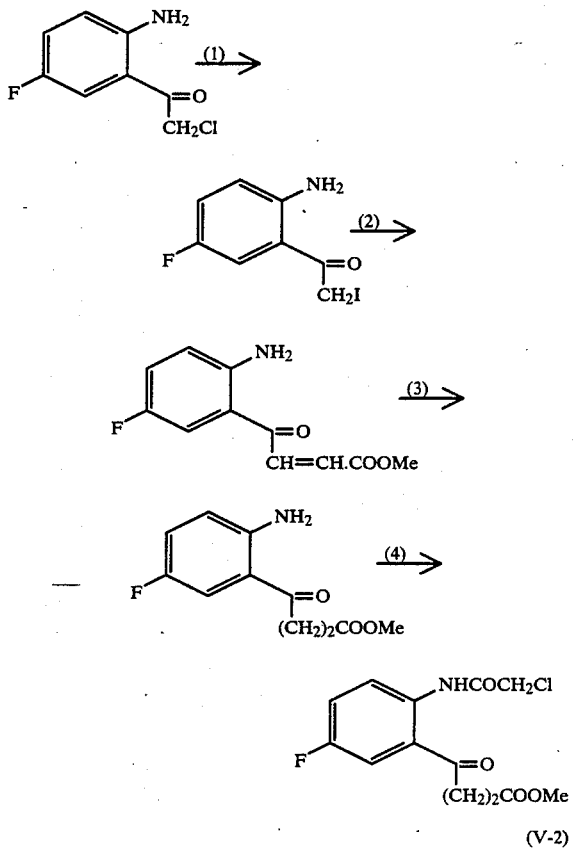

(1) To a solution of 23.463 g (125.069 mM) of 2'-amino-2-chloro-5'-fluoroacetophenone in 436 ml of CH₃CN is added 56.2 g (375.2 mM) of NaI, and the mixture is stirred at room temperature for 45 min. and concentrated under reduced pressure. The resulting residue is dissolved in ethyl acetate, washed with aqueous Na₂S₂O₃, and brine in order, dried and concentrated to give 29.97 g (Yield: 85.9%) of 2'-amino-5'-fluoro-2-iodoacetophenone as yellow crystals.

(2) To a solution of 29.97 g (107.40 mM) of 2'-amino-5'-fluoro-2-iodoacetophenone in 500 ml of benzene is added 71.82 g (214.8 mM) of triphenylphosphine carbomethoxymethylene, and the mixture is stirred at room temperature for 50 minutes and 1 hour. After removal of precipites, the filtrate is chromatographed on a column of silica gel (462.3 g), eluting with toluene-ethyl acetate (30:1-19:1 v/v) to give 10.9 g of crude product. This is recrystallized from Et₂O-n-hexane-CH₂Cl₂ to give 9.344 g (Yield: 39.0%) of methyl 4-(2-amino-5-fluorophenyl)-4-oxo-2-butenoate melting at 80°–84° C. as needles.

IR ν (CHCl₃): 3500, 1728, 1656, 1619, 1591, 1553, 1483, 1438 cm⁻¹

NMR (200 MHz) δ (CDCl₃): 3.851 (s, 3H); 6.667 (d-d, J₁=9.0 Hz, J₂=4.6 Hz, 1H); 6.821, 7.908 (ABq, J=15.4 Hz, 2H); 7.112 (d-d, J₁=9.6 Hz, J₂=9.0 Hz, J₃=2.8 Hz, 1H); 7.432 (d-d, J₁=9.6 Hz, J₂=2.8 Hz, 1H)

(3) A solution of 9.342 g (41.854 mM) of methyl 4-(2-amino-5-fluorophenyl)-4-oxo-2-butenoate in 200 ml of dioxane is hydrogenated in the presence of 10% of Pd-C at room temperature under atmospheric pressure. The reaction mixture is concentrated after removal of the catalyst. The resulting residue is chromatographed on a column of silica gel (463 g), eluting with toluene-ethyl acetate (19:1 v/v) to give 8.47 g of methyl 4-(2-amino-5-fluorophenyl)-4-oxobutyrate as orange crystals. Recrystallization from CH₂Cl₂-Et₂O-n-hexane gives 7.615 g (Yield: 80.8%) of the objective compound melting at 102°–103° C. as white needles.

Anal Calcd. (%) for C₁₁H₁₂FNO₃: C, 58.66; H, 5.37; N, 6.22; F, 8.44

Found (%): C, 58.56; H, 5.48; N, 6.24; F, 8.30

IR ν (CHCl₃): 3690, 3508, 3367, 1736, 1657, 1590, 1556, 1488, 1438, 1429 cm⁻¹

NMR (200 MHz) δ (CDCl₃): 2.720 (t, J=6.6 Hz, 2H); 3.260 (t, J=6.6 Hz, 2H); 3.717 (s, 3H); 6.624 (d-d, J₁=9.2 Hz, J₂=4.6 Hz, 1H); 7.046 (d-d-d, J₁=9.8 Hz, J₂=9.2 HZ, J₃=3 Hz, 1H); 7.441 (d-d, J₁=9.8 Hz, J₂=3.0 Hz, 1H)

(4) To a solution of 7.580 g (33.656 mM) of methyl 4-(2-amino-5-fluorophenyl)-4-oxobutyrate in 81 ml of CH₂Cl₂ is added 3.22 ml (40.387 mM) of chloroacetyl chloride, and the mixture is stirred at room temperature for 20 minutes and 1 hour. The reaction mixture is poured into aqueous NaHCO₃ under ice-cooling, and extracted with CH₂Cl₂. The CH₂Cl₂ layer is washed with water, dried and concentrated. The resulting residue in 10.23 g is recrystallized from CH₂Cl₂-Et₂O-n-hexane to give 9.321 g (Yield: 90.9%) of the objective compound (V-2) melting at 109.5°–110.5° C. as yellow needles.

Anal Calcd. (%) for C₁₃H₁₃ClFNO₄: C, 51.75; H, 4.34; N, 4.64; Cl, 11.75; F, 6.30

Found (%): C, 51.50; H, 4.43; N, 4.71; Cl, 11.90; F, 6.24

IR ν (CHCl₃): 3697, 3240, 1736, 1670, 1619, 1596, 1522, 1439, 1418, 1410 cm⁻¹

NMR (200 MHz) δ (CDCl₃): 2.788 (t, J=6.6 Hz, 2H); 3.343 (t, J=6.6 Hz, 2H); 3.725 (s, 3H); 4.183 (s, 2H); 7.315 (d-d-d, J₁=9.4 Hz, J₂=9.2 Hz, J₃=3.0 Hz, 1H); 7.674 (d-d, J₁=9.2 Hz, J₂=3 Hz, 1H); 8.748 (d-d, J₁=9.4 Hz, J₂=5.2 Hz, 1H)

REFERENCE EXAMPLE 11

Methyl 4-(2-chloroacethylaminophenyl)-4-oxobutyrate (V-3)

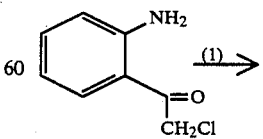

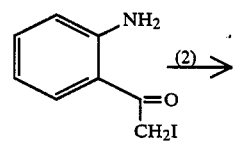

-continued

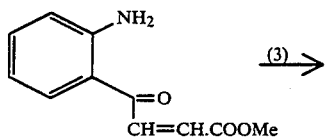 (3)→

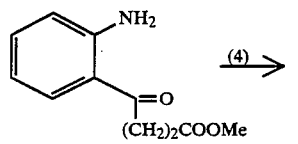 (4)→

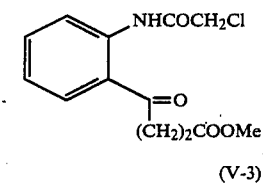
(V-3)

(1) To a solution of 33.11 g (195.21 mM) of 2'-amino-2-chloroacetophenone in 680 ml of $CH_3CN$ is added 87.8 g (585.63 mM) of NaI, and the mixture is stirred at room temperature for 45 minutes and concentrated under reduced pressure. The residue is dissolved in ethyl acetate, and the organic layer is washed with aqueous $Na_2S_2O_3$, and brine in order, dried and concentrated to give 46.1 g (Yield: 90.5%) of 2'-amino-2-iodoacetophenone as crystals.

(2) A solution of 46.1 g (176.59 mM) of 2'-amino-2-iodoacetophenone in 870 ml of benzene is added 118.1 g (353.172 mM) of triphenylphosphine carbomethoxymethylene, and the mixture is stirred at room temperature for 5 hours. After removal of the precipitate, the filtrate is chromatographed on a column of silica gel (750 g), eluting with toluene-ethyl acetate (30:1-19:1 v/v) to give 27.38 g (Yield: 75.6%) of methyl 4-(2-aminophenyl)-4-oxo-2-butenoate as red crystals.

IR $\nu$ ($CHCl_3$): 3495, 3345, 1722, 1649, 1618, 1581, 1542, 1481, 1450, 1438 $cm^{-1}$

NMR (90 MHz) $\delta$ ($CDCl_3$): 3.79 (s, 3H); 6.78, 7.96 (ABq, J=15 Hz, 2 Hz): 6.52–6.68 (m, 2H); 7.15–7.35 (m, 1H); 7.60–7.80 (m, 1H); 5.95 (br, disappeared by adding $CD_3OD$, 2H)

(3) A solution of 4.87 g (23.73 mM) of methyl 4-(2-aminophenyl)-4-oxo-2-butenoate in 120 ml of methanol and 6 ml of water is hydrogenated in the presence of 974 mg of 10% Pd-C at room temperature under atmospheric pressure. After removal of the catalyst, the mixture is concentrated to give a residue, which is chromatographed on a column of silica gel (274 g), eluting with toluene-ethyl acetate (30:1-19:1 v/v) to give 3.746 g of methyl 4-(2-aminophenyl)-4-oxobutyrate as orange crystals. This is recrystallized from $Et_2O$-n-hexane to give 3.162 g (Yield: 64.3%) melting at 50.0°–51.0° C. as yellow crystals.

Anal Calcd. (%) for $C_{11}H_{13}NO_3$: C, 63.76; H, 6.32; N, 6.76

Found (%): C, 63.78; H, 6.36; N, 6.80

IR $\nu$ ($CHCl_3$): 3695, 3508, 3368, 1735, 1650, 1618, 1587, 1552, 1488, 1452, 1432, 1409 $cm^{-1}$

NMR (200 MHz) $\delta$ ($CDCl_3$): 2.719 (t, J=6.6 Hz, 2H); 3.318 (t, J=6.6 Hz, 2H); 3.714 (s, 3H); 6.6–6.7 (m, 2H); 7.2–7.32 (m, 1H); 7.774 (d-d, $J_1$=8.4 Hz, $J_2$=1.6 Hz, $J_3$=3 Hz, 1H); 7.441 (d-d, $J_1$=8.4 Hz, $J_2$=1.6 Hz, 1H)

(4) A solution of 3.737 g (18.03 mM) of methyl 4-(2-aminophenyl)-4-oxobutyrate in 43 ml of $CH_2Cl_2$ is added 1.724 ml (21.64 mM) of chloroacetyl chloride. After stirring at room temperature for 15 minutes and 1 hour, the reaction mixture is poured into aqueous $NaHCO_3$ under ice-cooling. The $CH_2Cl_2$ layer is washed with water, dried, and concentrated. The resulting residue in 5.086 g is chromatographed on a column of silica gel (234.6 g), eluting with toluene-ethyl acetate (30:1-9:1 v/v) to give 5.00 g of yellow crystals. This is recrystallized from $CH_2Cl_2$-$Et_2O$-n-hexane to give 4.797 g (Yield: 93.8%) of methyl 4-(2-chloroacetylaminophenyl)-4-oxobutyrate (V-3) melting at 101.5°–102.0° C. as pale yellow needles.

Anal Calcd. (%) for $C_{13}H_{14}ClNO_4$: C, 55.04; H, 4.97; N, 4.94; Cl, 12.50

Found (%): C, 54.78; H, 4.88; N, 4.93; Cl, 12.44

IR $\nu$ ($CHCl_3$) $cm^{-1}$: 3692, 3230, 1737, 1687, 1664, 1608, 1587, 1523, 1452, 1439, 1411

NMR (200 MHz) $\delta$ ($CDCl_3$): 2.784 (t, J=6.6 Hz, 2H); 3.398 (t, J=6.6 Hz, 2H); 3.722 (s, 3H); 4.188 (s, 2H); 7.169–7.267 (m, 1H); 7.553–7.640 (m, 1H); 8.013 (d-d, $J_1$=8.0 Hz, $J_2$=1.6 Hz, 1H); 8.734 (d-d, $J_1$=8.4 Hz, $J_2$=1.2 Hz, 1H)

| Preparation | |
|---|---|
| 8-Acetyl-3,5,11-trioxo-1H-pyrrolo-[2,1-c][1,4]benzodiazepine | 10 mg |
| Wheat starch | 48 mg |
| Magnesium stearate | 2 mg |

The above ingredients are admixed to prepare a capsule.

Effect of the Invention

The compounds of the present invention (I) showed good activity against amnesia introduced by electroconvulsive shock.

Compound numbers in Experiment correspond to those in Examples and/or Tables.

EXPERIMENT

Prevention against the ECS-Induced Amnesia in Mice

The test apparatus was a black acrylic resin box (30×30×30 cm) with an electrifiable grid floor in which a white wooden platform (10×10×1 cm) was placed in one corner. The step-down passive avoidance test was conducted on 3 groups of 10 DS mice (male, 4 to 5 weeks age). A solvent was orally administered to the animals of the first group for control and the test compound at doses of 5 and 50 mg/kg were orally given to other 2 groups 60 min. before the acquisition trial. In the acquisition trial, mice were individually placed on the platform and a scrambled foot shock (3 mA, for 5 sec.) was delivered through the grid floor as soon as the mouse moved off the platform. Five to ten min. after the foot shock, a single electroconvulsive shock (30 mA, 100 Hz (rectangular wave of 1 msec duration), for 0.2 sec.) was applied transcorneally and at once each animal was placed in the home cage. After 24 hr., each mouse was again placed on the platform and the latency for descending on the grid floor was measured. A long latency in the retention test indicates good acquisition. The step-down latencies were evaluated by the Mann-Whitney U-test.

In Table 3, the results were shown as percent change in latencies over control defined as 100.

TABLE 3

Effects of Compounds against Amnesia Induced by Electro-Convulsive Shock

| Compound No. | 5 mg/kg | 50 mg/kg |
|---|---|---|
| I a-7 | 144* | 163* |
| I b-2 | 190** | 74 |
| I c-2 | 124 | 241** |
| I c-3 | 216** | 151 |
| I c-8 | 113 | 245*** |

*$p < 0.05$,
**$p < 0.025$,
***$p < 0.01$

What we claim is:

1. A compound of the formula:

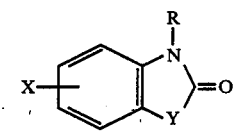 (I)

wherein Y is

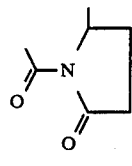 (a)

or

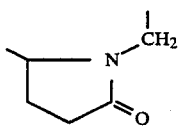 (b)

R is hydrogen, $C_1$–$C_5$ alkyl, $C_1$–$C_5$ alkanoyl, or $C_7$–$C_9$ phenylalkyl, and X is hydrogen, $C_1$–$C_5$ alkoxy, or halogen.

2. A compound claimed in claim 1, in which said compound is represented by the formula:

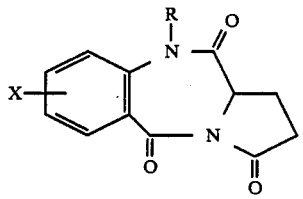

wherein R is hydrogen, $C_1$–$C_3$ alkyl, $C_1$–$C_3$ alkanoyl, or benzyl, and X is hydrogen, halogen, or $C_1$–$C_3$ alkanoyl.

3. A compound claimed in claim 2, namely 5-acetyl-1H-pyrrolo[2,1-c][1,4]benzodiazepine-1,4,10-trione.

4. A compound claimed in claim 2, namely 5-methyl-1H-pyrrolo[2,1-c][1,4]benzodiazepine-1,4,10-trione.

5. A compound claimed in claim 2, namely 5-propyl-1H-pyrrolo[2,1-c][1,4]benzodiazepine-1,4,10-trione.

6. A compound claimed in claim 2, namely 5-benzyl-1H-pyrrolo[2,1-c][1,4]benzodiazepine-1,4,10-trione.

7. A compound claimed in claim 2, namely 5-methyl-7-methoxy-1H-pyrrolo[2,1-c][1,4]benzodiazepine-1,4,10-trione.

8. A compound claimed in claim 2, namely 5-benzyl-7-methoxy-1H-pyrrolo[2,1-c][1,4]benzodiazepine-1,4,10-trione.

9. A compound claimed in claim 2, namely 5-methyl-7-fluoro-1H-pyrrolo[2,1-c][1,4]benzodiazepine-1,4,10-trione.

10. A compound claimed in claim 2, namely 5-benzyl-7-fluoro-1H-pyrrolo[2,1-c][1,4]benzodiazepine-1,4,10-trione.

11. A compound claimed in claim 2, namely 7-methoxy-1H-pyrrolo-[2,1-c][1,4]benzodiazepine-1,4,10-trione.

12. A compound claimed in claim 1, in which said compound is represented by the formula:

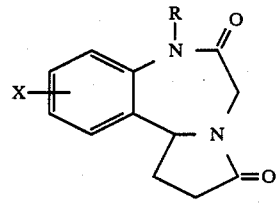

wherein R is hydrogen, $C_1$–$C_3$ alkyl, or benzyl, and X is hydrogen, and halogen.

13. A compound claimed in claim 12, namely 10-chloro-7,11b-dihydro-1H-pyrrolo[1,2-d][1,4]benzodiazepine-3,6-(2H,5H)-dione.

14. A compound claimed in claim 12, namely 10-chloro-7-methyl-7,11b-dihydro-1H-pyrrolo[1,2-d][1,4]benzodiazepine-3,6-(2H,5H)-dione.

15. A compound claimed in claim 12, namely 10-chloro-7-n-propyl-7,11b-dihydro-1H-pyrrolo[1,2-d][1,4]benzodiazepine-3,6-(2H,5H)-dione.

16. A compound claimed in claim 12, namely 7-benzyl-10-chloro-7,11b-dihydro-1H-pyrrolo[1,2-d][1,4]benzodiazepine-3,6-(2H,5H)-dione.

17. A compound claimed in claim 12, namely 10-fluoro-7,11b-dihydro-1H-pyrrolo[1,2-d][1,4]benzodiazepine-3,6-(2H,5H)-dione.

18. A compound claimed in claim 12, namely 10-fluoro-7-n-propyl-7,11b-dihydro-1H-pyrrolo[1,2-d][1,4]benzodiazepine-3,6-(2H,5H)-dione.

19. A compound claimed in claim 12, namely 7-benzyl-10-fluoro-7,11b-dihydro-1H-pyrrolo[1,2-d][1,4]benzodiazepine-3,6-(2H,5H)-dione.

20. A compound claimed in claim 12, namely 7-n-propyl-7,11b-dihydro-1H-pyrrolo[1,2-d][1,4]benzodiazepine-3,6-(2H,5H)-dione.

21. A compound claimed in claim 12, namely 7-n-propyl-7,11b-dihydro-1H-pyrrolo[1,2-d][1,4]benzodiazepine-3,6-(2H,5H)-dione.

22. A compound claimed in claim 12, namely 7-methyl-7,11b-dihydro-1H-pyrrolo[1,2-d][1,4]benzodiazepine-3,6-(2H,5H)-dione.

23. A pharmaceutical composition for the treatment of senile dementia, psychoneurosis, and/or amnesia comprising a pharmacologically effective amount of a compound according to claim 1 together with a pharmaceutically acceptable carrier.

* * * * *